(12) United States Patent
Pertot et al.

(10) Patent No.: US 8,431,120 B2
(45) Date of Patent: Apr. 30, 2013

(54) *TRICHODERMA ATROVIRIDE* SC1 FOR BIOCONTROL OF FUNGAL DISEASES IN PLANTS

(75) Inventors: Ilaria Pertot, Tesero (IT); Claudia Maria Longa, Ischia di Pergine (IT); Daniele Prodorutti, Ravascletto (IT); Lorenza Michelon, Faedo (IT); Federica Savazzini, Parma (IT)

(73) Assignees: Trentino Sviluppo S.p.A., Rovereto (IT); Fondazione Edmund Mach, San Michele All'Adige (IT)

( * ) Notice: Subject to any disclaimer, the term of this patent is extended or adjusted under 35 U.S.C. 154(b) by 176 days.

(21) Appl. No.: 12/933,844

(22) PCT Filed: Mar. 21, 2008

(86) PCT No.: PCT/IT2008/000196
§ 371 (c)(1),
(2), (4) Date: Sep. 21, 2010

(87) PCT Pub. No.: WO2009/116106
PCT Pub. Date: Sep. 24, 2009

(65) Prior Publication Data
US 2011/0020286 A1   Jan. 27, 2011

(51) Int. Cl.
*A01N 63/00* (2006.01)
*C12N 1/00* (2006.01)

(52) U.S. Cl.
USPC ................................. 424/93.5; 435/256.7

(58) Field of Classification Search .................. None
See application file for complete search history.

(56) References Cited

U.S. PATENT DOCUMENTS

| | | | | |
|---|---|---|---|---|
| 4,713,342 A | * | 12/1987 | Chet et al. ..................... | 424/93.5 |
| 4,900,348 A | * | 2/1990 | Hoitink ............................ | 71/6 |
| 5,288,634 A | * | 2/1994 | Harman et al. ............. | 435/254.1 |
| 5,422,107 A | * | 6/1995 | Kubota ........................ | 424/93.5 |
| 6,750,176 B2 | * | 6/2004 | Misumi et al. ................ | 504/117 |
| 6,890,530 B2 | * | 5/2005 | Hermosa Prieto et al. .. | 424/93.5 |
| 2004/0067851 A1 | * | 4/2004 | Misumi et al. ................ | 504/117 |
| 2004/0121442 A1 | * | 6/2004 | Chet et al. ..................... | 435/200 |
| 2004/0265953 A1 | * | 12/2004 | Harman et al. .............. | 435/69.1 |
| 2006/0021470 A1 | * | 2/2006 | Lorito et al. ..................... | 75/710 |

FOREIGN PATENT DOCUMENTS

| | | |
|---|---|---|
| EP | 0 466 133 | 1/1992 |
| EP | 1 876 232 | 1/2008 |
| FR | 2 813 758 | 3/2002 |

OTHER PUBLICATIONS

Harvey et al. New Zealand Plant Protection 59:343-347 (2006).*
Elad, *Biological control of foliar pathogens by means of Trichoderma harzianum and potential modes of action*, Crop Protection, vol. 19, No. 8-190, Sep. 2000, pp. 709-714.
Elmer et al., *Biosuppression of Botrytis cinerea in grapes*, Plant Pathology, vol. 55, No. 2, Apr. 2006, pp. 155-177.
Savazzini et al., *Real-time PCR for detection and quantification of the biocontrol agent trichoderma atroviride strain SC1 in soil*, Journal of Microbiological Methods, vol. 73, No. 2, May 2008, pp. 185-194.
Longa et al., *Ecophysiological requirements and survival of a Trichoderma atroviride isolate with biocontrol potential*, Journal of Basic Microbiology, vol. 48, No. 4, Aug. 2008, pp. 269-277.
International Preliminary Report on Patentability dated Jan. 7, 2010.
Written Opinion dated Dec. 3, 2008.
International Search Report dated Dec. 3, 2008.

* cited by examiner

*Primary Examiner* — Chris R Tate
*Assistant Examiner* — Douglas F White
(74) *Attorney, Agent, or Firm* — Ohlandt, Greeley, Ruggiero and Perle, L.L.P.

(57) ABSTRACT

An embodiment of the present invention is a *Trichoderma atroviride* SC1, CBS n° 122089, as a biocontrol agent, i.e. to treat fungal diseases of plants. The second embodiment of the present invention is an agricultural composition comprising the *Trichoderma atroviride* SC1 as the active principle in an effective amount. The compositions of the present invention may further comprise a second biocontrol agent and/or an additive, an emulsifier, a plant nutrient, a wetting-agent, a plant micro-nutrient or a substratum, wherein said substratum is selected from the group consisting of: a nutrient culture medium, a cereal or a derivative thereof, an amendant, a vegetable or a part thereof, peat, wood or a piece thereof, clay or barks.

23 Claims, 12 Drawing Sheets

Figure 8 A
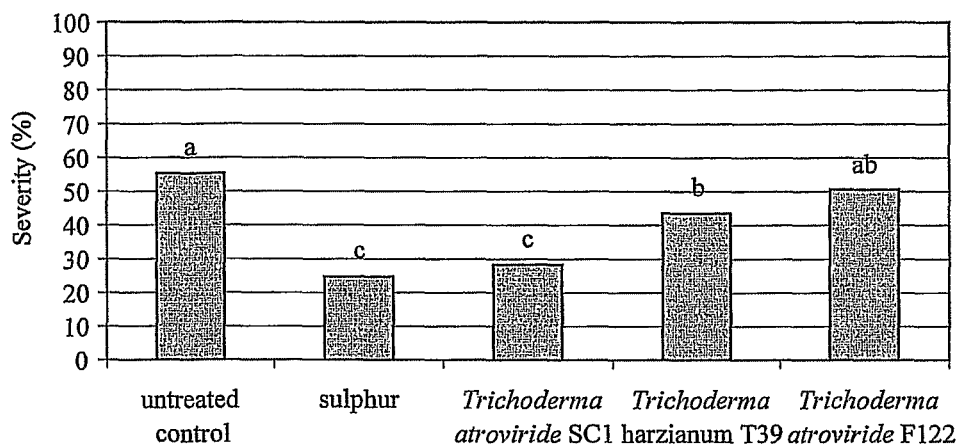
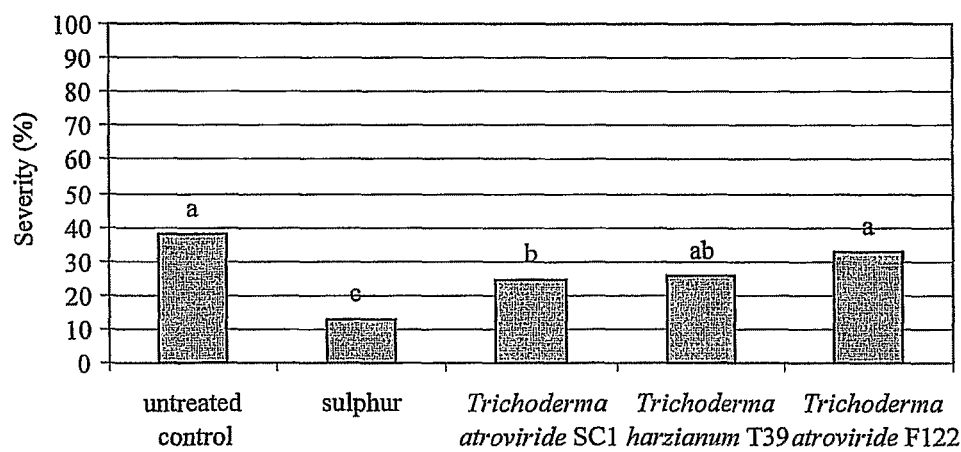
Figure 8 B

Figure 9 A
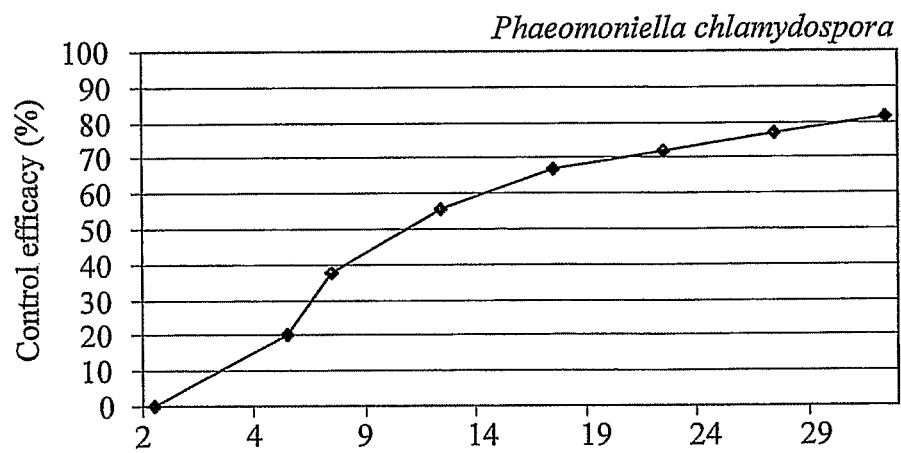
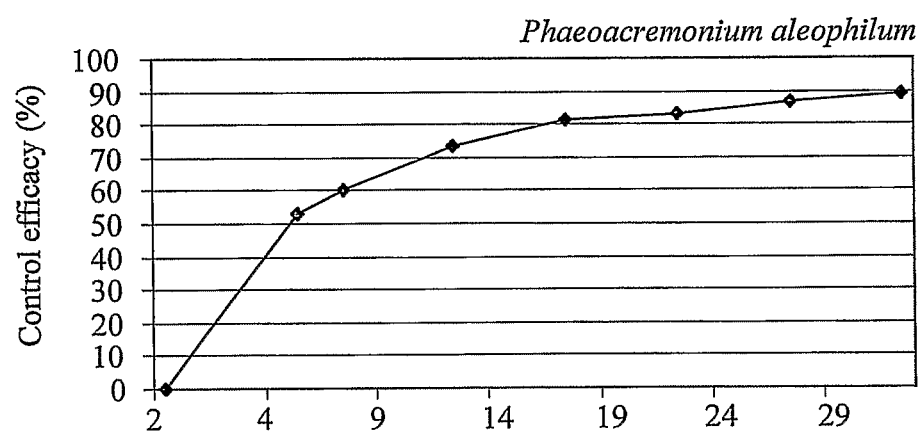
Figure 9 B

TRICHODERMA ATROVIRIDE SC1 FOR BIOCONTROL OF FUNGAL DISEASES IN PLANTS

FIELD OF THE INVENTION

The field of the present invention is the biological control of plant diseases caused by pathogenic Fungi by a biocontrol agent, represented by a novel *Trichoderma atroviride* strain.

BACKGROUND OF THE INVENTION

Replacement or reduction of chemical fungicides has been achieved through the use of biologically based fungicides, an approach falling within the definition of Biological Control as proposed by Cook and Baker (1983): "Biological control is the reduction of the amount of inoculum or disease-producing activity of a pathogen accomplished by or through one or more organism other than man". This broad definition includes use of less virulent variants of the pathogen, more resistant cultivars of the host, and microbial antagonists "that interfere with the survival or disease-producing activities of the pathogen".

A more complex evaluation of the environmental interactions is required to use such Biocontrol Agents (BCAs). In fact environmental conditions affect not only the survival of BCAs, but also their efficacy against pathogens (Paulitz, 2000). BCAs that are more flexible in terms of environmental adaptation can be more easily developed into commercial products, as their applications and target markets can be wider than those of BCAs requiring specific environmental conditions.

The selection of antagonistic *Trichoderma* strains with enhanced tolerance to unfavorable environmental conditions can increase the reliability of *Trichoderma*-based biocontrol programs (Kredics et al., 2000). It is also important to note that the most effective BCAs for use against plant pathogens are those that have better stress tolerance than their target pathogens (Kredics et al., 2000; 2004). *Trichoderma* is a cosmopolitan genus, which can colonize soils, rhizospheres and phyllospheres. *Trichoderma* species are frequently found on decaying wood and vegetable material. Several *Trichoderma* strains are economically important producers of industrial enzymes.

*Trichoderma* strains have been already used as biocontrol agents against numerous plant pathogens and quite a few have been developed for use as commercial (i.e *Trichoderma harzianum*, known as Trichodex®) biocontrol products for field and greenhouse crops (Elad, 2000; Harman, 2000).

However a great variability exists in terms of biocontrol activity, specificity, mechanism of action, production of metabolites and survival in soil or on plant among *Trichoderma* species, which affect their use as BCAs (Benitez et al., 2004). Moreover there are still several important pathologies, such as those caused by the *Armillaria* genus on grapevine for which fully effective biocontrol agents have neither been isolated nor characterized.

BRIEF DESCRIPTION OF THE DRAWINGS

FIG. 8. Effect of *Trichoderma atroviride* SC1 on the severity of powdery mildew infection. Cucumber (panel A) and zucchini (panel B) plants artificially inoculated with *Podosphaera xanthii* conidia and comparison with untreated, sulphur and two biocontrol standards (*Trichoderma harzianum* T39—commercial name Trichodex®—and *T. atroviride* F122). The assessments were made two weeks after inoculation scoring severity (percentage of infected leaf tissue). Five replicates (plants) per treatment were rated. Columns with the same letter are not significantly different according to Tukey's HSD (P≦0.05). For the artificial inoculation, approximately 5 ml of an aqueous suspension of conidia ($10^7$ conidia ml$^{-1}$) were sprayed on each plant. Daily applications started 12 hours after inoculation.

*atroviride* SC1 were done on potato dextrose agar in Petri dishes. The graphs represent the average of five replicates (Petri dishes).

Figure 10:
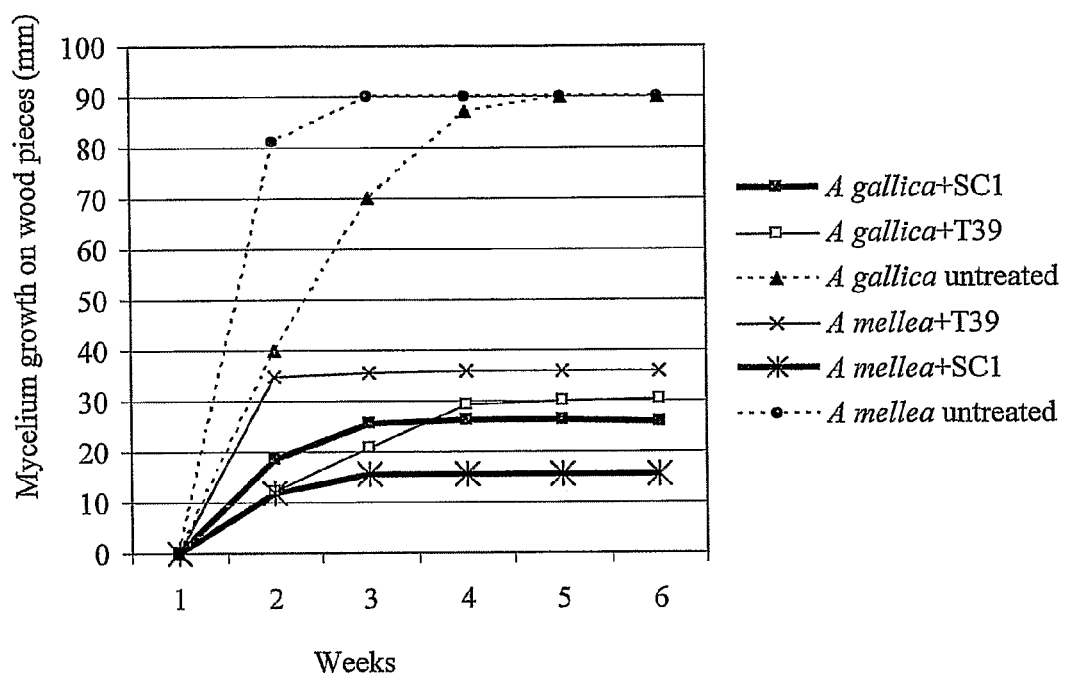

FIG. 10. Myceliar growth of *Armillaria mellea* and *Armillaria gallica* (root rot causal agents) in presence of *Trichoderma atroviride* SC1 and without (untreated). The experiment Effect of *Trichoderma harzianum* T39—Trichodex® is presented herein as standard comparison. The growth is expressed as average of diameter of five replicates grown on wood pieces on PDA on Petri dishes at 20° C.

Figure 11:
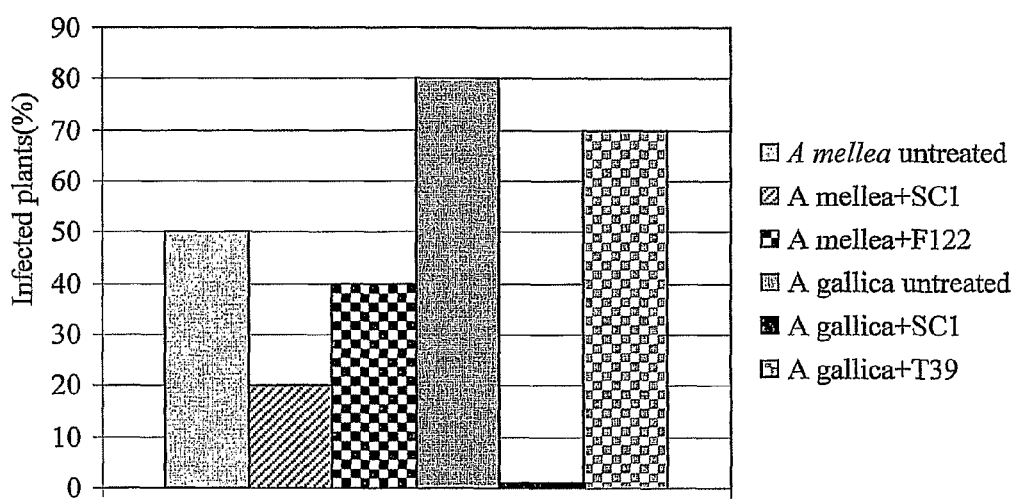

FIG. 11. Percentage of *Armillaria mellea* and *A. gallica* infected (dead) strawberry plants after soil treatment. The effect of *Trichoderma atroviride* SC1 was compared to the untreated. *Trichoderma harzianum* T39—Trichodex®—was used as comparison for the *A. gallica* and *T. atroviride* F122 it is used as comparison for *A. mellea*. The values are percentages calculated on 10 replicate plants.

SUMMARY OF THE INVENTION

An embodiment of the present invention is a *Trichoderma atroviride* SC1, CBS n° 122089, as a biocontrol agent, i.e. to treat fungal diseases of plants.

The second embodiment of the present invention is an agricultural composition comprising the *Trichoderma atroviride* SC1 as the active principle in an effective amount. The compositions of the present invention may further comprise a second biocontrol agent and/or an additive, an emulsifier, a plant nutrient, a wetting-agent, a plant micro-nutrient or a substratum, wherein said substratum is selected from the group consisting of: a nutrient culture medium, a cereal or a derivative thereof, an amendant, a vegetable or a part thereof, peat, wood or a piece thereof, clay or barks.

A further embodiment is a method for treating or preventing a plant disease caused by a pathogenic fungus selected from the group of those causing: wood diseases (*Phaeomoniella chlamydospora, Phaeoacremonium aleophilum* and *Fomitiporia mediterranea*), foliar diseases (the powdery mildew causative agent *Podosphaera xanthii*), fruit and flower diseases (*Botrytis cinerea*) and root diseases caused by *Armillaria* genus (*Armillaria mellea* and *A. gallica*).

Treatment can be carried out directly on the plant or on a plant part, or indirectly by applying *Trichoderma atroviride* SC1, CBS n° 122089 enriched substrata in the soil or on it, in close proximity of the plant. Plants which benefit from this treatment are preferably selected from the group consisting of: Cucurbitaceae, Rosaceae, Vitaceae, Crucifereae, Compositae, Ubelliferae, Solanaceae and Liliaceae.

Further embodiments of the present invention are substrata comprising an effective amount of the microorganism *Trichoderma atroviride* SC1 or treated with compositions comprising an effective amount of said strain. A preferred substratum is represented by bark or boiled rice.

A further embodiment is represented by a molecular method for the specific detection of *Trichoderma atroviride* SC1 where parallel amplification of Endochitinase 42 gene (ech42) GenBank Acc N° AB041753.1 and of a G protein α subunit gene (tga3) GenBank Acc N° AF452097.1 is achieved with suitable primer sets and wherein in a sample comprising said *Trichoderma atroviride* SC1 two polymorphic nucleotides in position 185 and 196 of the Endochitinase 42 gene are observed.

DETAILED DESCRIPTION OF THE INVENTION

An object of the present invention is to provide a biocontrol agent belonging to the *Trichoderma atroviride* species, strain SC1, for the suppression of development of fungal diseases on aerial part of the plants and on roots.

According to a preferred embodiment, *Trichoderma atroviride*, strain SC1 has been deposited on Nov. 27, 2007, under the Budapest Treaty at the CBS (Centraalbureeau voor Schimmelcultures) under N° CBS 122089.

According to the main aspect of the present invention *Trichoderma atroviride*, strain SC1 is proposed to suppress and to prevent the development of plant pathogens, in particular: fruits and root rots, such as those caused by *Botrytis cinerea* and *Armillaria* spp., powdery mildews, wood diseases (Esca disease), According to a preferred embodiment the invention provides a method of suppressing or preventing development of fungal diseases on plants characterized for using compositions comprising an effective amount of *Trichoderma atroviride* SC1, in a quantity of at least $10^2$-$10^3$ conidia $ml^{-1}$ or $g^{-1}$ when solid composition are used.

*Trichoderma atroviride* SC1 is a mesophilic fungus as most *Trichoderma* spp. (Klein and Eveleingh, 1998.) It is able to utilize a wide range of compounds as sole carbon and nitrogen sources. Fungal growth in culture media is superior with some nitrogen sources such Yeast Extract, Nitrite, Tryptone, Peptone, Glutamine and Asparagine or some carbon sources such Mannose, Galactose, Sucrose, Malt Extract, Cellobiose Glucose and Threalose.

*T. atroviride* SC1 survives in a temperature range comprised from −1 and 35° C. and grows in a range of temperatures comprised from 5 to 30° C. The optimal temperature for growth is 25° C.±1° C., although fungal radial growth at 20° C. is not significantly different than the growth observed at 25° C. The maximum temperature for *T. atroviride* SC1 survival (30° C.) is lower than human body temperature, which is a good indication that this fungus is not pathogenic to humans.

The pH tolerance levels of *T. atroviride* SC1 fall within the common range for *Trichoderma* strains, i.e. a pH range comprised from 3 to 10. The minimum limit of water activity tolerance ($a_w$) of *T. atroviride* SC1 is 0.910. The preferred value of water activity is 0.998, which correspond to values of high relative humidity conditions preferred by most of the fungal plant pathogens (90-100%). *Trichoderma atroviride* SC1 is characterized by the following properties:

it is particularly active against diseases caused by *Armillaria* spp. and against the causal agents of the "esca disease" for which no effective chemical pesticides are known. According to the invention, the term *Armillaria* spp. covers in particular *Armillaria mellea* and *Armillaria gallica*, the term "esca disease" covers the most important pathogens causing esca disease, in particular *Phaeomoniella chlamydospora, Phaeoacremonium aleophilum* e *Fomitiporia mediterranea. Armillaria* spp. affects more than 400 plant species (crops and forest trees). "Esca disease" pathogens affect grapevine.

it is more effective against Powdery mildew (caused by *Podosphaera xanthii*) than other known *Trichoderma* strains, such as *Trichoderma harzianum* T39 (commercial name Trichodex®) or *T. atroviride* F122 (Longa, 2007). Powdery mildews are fungal diseases caused by many different species of fungi in the order Erysiphales (Spencer, 1978) and cause economically important damages in particular to grape, apple, strawberry, horticultural and floricultural crops;

it persists in soil at effective levels for long periods (more than one year)

it can be easily dispersed on vegetable or wood parts, where it survives as an antifungal agent for more than one year.

Several tests carried out with *T. atroviride* SC1, which will be better detailed in the experimental part, allow it to be proposed as an optimal biocontrol agent for suppression of fungal diseases on plants.

According to a preferred embodiment, the preparation of *T. atroviride* SC1 agricultural compositions is carried out by inoculating *T. atroviride* SC1 (few spores washed from culture plates are usually enough) on a common nutrient substrate in liquid suspension or on solid substrate to obtain at least $10^2$-$10^3$ conidia/ml$^{-1}$ or g$^{-1}$ of substrate (active concentration).

The most commonly used liquid or semisolid media comprises: nutrient broth, potato dextrose agar (PDA) nutrient agar, malt extract agar, malt agar, LB broth and similar known to the skilled man, where fungi are grown under continuous shaking, for at least 48, preferably 72 hours or until conidia are produced, at an optimal growing temperature comprised from 20 to 30° C. or preferably from 22 to 26° C. or at about 25° C.±1° C., for at least 48 h. In these conditions the first conidia are produced after at least 48 hrs.

A preferred solid substrate comprises a sterilised cereal (such as boiled rice or wheat), flour or grinded cereals, or a similar carbohydrate-rich substrate, where *T. atroviride* SC1 is inoculated and incubated for at least one week from 20 to 30° C. or preferably from 22 to 26° C. or about 25° C.±1° C. Cereal derivatives such as flour or grinded cereals are suitable as well.

Plant treatment and for prevention is carried out by using *T. atroviride* SC1 cultures grown in liquid or semi-solid media or on a solid substrate and applying such *T. atroviride* SC1 suspension onto parts of the plant or applying the SC1-enriched substrate on or into the soil in close proximity of the plant in need of such a treatment.

Treatment can be carried out by, applying agricultural compositions to plants, on the leaves of plants, on wounds made during cutting or pruning, or to the soil to suppress the development of fungal diseases on roots. Treatments are applied by spray on plants as a common fungicide, with a timing that should be adapted to the specific disease (i.e. before infection, at a specific phenological stage of plants such as transplanting, bloom, post-harvest). Treatments can be also sprayed or injected in the soil, mixed with the soil on several substrates and different formulations (i.e. granules, mixed with clay or similar products, barks, vegetable or other organic matter or similar or derivatives). Treatments can be applied during plant vegetative period or during dormancy. The treatment can be sprayed after pruning or applied directly to the pruning wounds to prevent infections. Treatments can be applied weekly or more frequently, as well as once in a year. The treatment can be applied once (i.e. at planting time in soil) o repeated as needed.

A high persistence in soil and the easiness of dispersion on solid supports such as barks renders the present microorganism particularly suitable for treating plants and/or areas comprising plants, minimizing number of treatments.

By culture substratum is meant an organic culture support which can be either liquid, solid, semisolid (gelly) and which can be organic such as rice, bark or wood pieces or vegetable amendants, such as peat, or inorganic (i.e. mineral) such as clay. Substrata may have either a nutrient or a matrix function, or both. Wood pieces, barks or inorganic substrata are preferably pre-treated with a nutrient before SC1 inoculation.

Of note, growth on bark pieces is not possible with other *T. atroviride* strains, such as the 122F strain. Therefore this embodiment represents a further distinguishing feature of the SC1 strain according to the present invention.

*T. atroviride* SC1 conidia can be also collected (i.e. by an air flux or by washing a culture substrate) and dispersed into a liquid or a liquid nutrient. Such a suspension, or agricultural composition, is applied directly to the plant or to the soil in close proximity to the plant. It is preferably applied in combination with nutrients such as a carbon source (i.e. a sugar) and a nitrogen source, such as aminoacids, peptides, nutrient factors or plant micronutrients for a better maintenance of the microorganism in situ.

The composition may further comprise emulsifiers, such as lecithin, saponins, wetting agents, such as Tween 80, or similar, UV protectors, antioxidants with emulsifiers, diluents, wetting agents, spray adjuvants. For the purposes of the present invention any culture substratum either solid or liquid, comprising an effective amount $10^2$-$10^3$ conidia ml$^{-1}$ or g$^{-1}$ of the *T. atroviride* SC1 is considered an agricultural composition.

Suspensions or compositions comprising at least $10^2$-$10^3$ ml$^{-1}$ or g$^{-1}$ conidia are applied directly on the plant or plant parts, such as roots, leaves, seeds or fruit, or indirectly to the soil, preferably on the above solid supports.

In the above agricultural compositions, the SC1 strain can be optionally mixed with a second or further biocontrol agents, supplements, fertilizers, minerals, plant hormones, amenders for plant growth, chemical pesticides non toxic to *T. atroviride* SC1 or waxes for protecting pruning wounds in irrigation water. One of the most preferred method for treating soil with *T. atroviride* SC1 is to allow this strain to grow on a substrate such as a cereal, (i.e. boiled rice), or bark or wood pieces or vegetable amenders such as peat and distributing said supports on or into the soil in close vicinity to the plant/plants to be treated.

Growth of an effective amount of *T. atroviride* SC1 culture ($10^2$-$10^3$ conidia ml$^{-1}$ or g$^{-1}$) on such solid substrate (i.e. bark pieces) is preferably carried out by pre-treating it with a microbiological media (such as potato dextrose broth, malt extract, nutrient broth or similar) or any nutrient substance containing a carbon and a nitrogen source (such as beef extract, peptone, grinded cereals, yeast extract, sucrose or similar), inoculating such substratum with *T. atroviride* SC1 and incubating it in the condition described above for at least one week or until colonization is obtained.

Composition may be also prepared by washing conidia out of the infected plates or culture substrates and spraying such suspensions on the aerial parts of the plant before pathogen infection, weekly, at some specific plant phenological stage or after some agricultural practices such as pruning, cutting, planting.

Plants to which the composition are successfully applied, are preferably selected from the group consisting of: Cucurbitaceae, Rosaceae, Vitaceae, Crucifereae, Compositae, Ubelliferae, Solanaceae and Liliaceae. Particularly preferred plants are Cucurbitaceae, Rosaceae, Vitaceae.

Treatment, either by an inoculated solid substratum (i.e. barks or vegetable amenders) or by other means such as spraying, is carried out at any time of plant cultivation to provide control of existing soilborne pathogens or to prevent new infections.

A preferred method for rhyzosphere treatment with the biocontrol agent of the present invention is achieved by growing *T. atroviride* SC1 in sterilized boiled rice (or another cereal) for few days (minimum one week, usually 15 days) at a temperature comprised within the optimal range, preferably at about 25° C.±1° C., until an optimal inoculum dose in the range of $10^7$-$10^8$ conidia/100 g boiled rice or $1 \times 10^6$ cfu g$^{-1}$ soil is obtained. According to this embodiment the biocontrol agent is applied directly as a fungi-enriched rice matrix.

In order to monitor the fate and behavior of a released microorganism in the environment, which is of utmost importance for the control of BCA, a molecular approach (Real Time PCR) has been developed and represents a further embodiment of the present invention.

This method allows tracking and quantifying *T. atroviride* SC1 in the environment, specifically identifying the released strain, distinguishing it from the native microbial community and tracking its population dynamic over time.

In fact, registration of a specific biocontrol agent (BCA) as a pesticide in Europe requires a risk assessment focused on the persistence and multiplication of the BCA in the environment, in addition to an evaluation of any possible contamination (viable and non-viable BCA residues) of foodstuffs.

The molecular test developed according to a further embodiment of the present invention is based on the *T. atroviride* SC1 endochitinase gene (ech42) (Carsolio et al., 1994) Therefore, the real-time PCR primers and the strain-specific TaqMan probe set (Sigma Aldrich, St. Louis, Mo.) were designed based on two nucleotide mismatches on the 3' strand of the ech42 gene, in position 185 and 196 according to the numbering of the GenBank Acc.AB041753.1 sequence. A second primer set and TaqMan probe were designed for the tga3 gene, which encodes the G protein $\alpha$ subunit (Table 1).

PCR using the ech42 and tga3 primers resulted in specific amplification products from all DNA from *Trichoderma* spp. strains, but not other fungi from soil samples (i.e. *Asperigillus* spp. *Penicillium* spp. *Cladosporium* spp.). The products gave a single melting peak for each gene, which indicates that the primers only amplified ech42 and tga3 products.

Conversely, when Real Time PCR is carried out also in the presence of a ech42 TaqMan probe containing the two SC1-specific point mutations of the ech42 gene sequence (preferably SEQIDNO 3) only *T. atroviride* SC1 produces a single signal and no probe amplification product hybridization occurs for the other fungi (strain F122 and SB18 included) in grapevine and soil samples, confirming the high specificity of the ech42 probe.

Duplex amplification of the ech42 and tga3 TaqMan probe for the series of concentrations of *T. atroviride* SC1 DNA occurred at the same threshold for each given concentration. This demonstrates that there is a single copy of the ech42 amplicon in the genome and a single copy of the Tga3 gene, and that these two sequences have similar standard curves so that they represent suitable amplification primer sets, as confirmed by the fact that PCR reactions for each of these two sequences proceeded with similar levels of efficiency (FIG. 4).

This method yields a limit of detection (LOD) and limit of quantification (LOQ) of 5 genome copies per PCR reaction. For the soil samples, the calculated LOD increased to 35 copies per reaction mixture, equivalent to $6.2\times10^3$ conidia per g soil, and LOQ ranged from $2\times10^4$ to $3\times10^4$ g $soil^{-1}$. The accuracy of the method is very high at the five tested conidial concentration levels as shown in the Experimental Part. The skilled man starting from the allelic variations in the Ech42 P identified in the present method can easily identify alternative primer sets and different probes still comprising the two identified mismatches specific for the SC1 strain. Also, different molecular probes are possibly linked to the probe and/or primer.

Real-time PCR primers and probes designed for the detection and quantification of *T. atroviride* SC1 are shown in the table below. The base mismatches in the ech42 TaqMan probe are in bold.

| Primers and probes | Sequence (5'-3') | Amplified product (bp) |
|---|---|---|
| | Endochitinase 42 gene (ech42) | |
| Ech42 Fw | GTTCTGAGGCTGGAAGTTGC SEQ ID NO 1 | |
| Ech42 Rv | ACGCCGTCTACTTCACCAAC SEQ ID NO 2 | |
| Ech42 P | 6FAM-TACCCCTTCAATCACCAATTGTTAG-TAMRA SEQ ID NO 3 | 112 |
| | G protein a subunit gene (tga3) | |
| Tga3 Fw | TGTTGAAGCATTGGGTTTGA SEQ ID NO 4 | |
| Tga3 Rv | TGATTGAGGTGACGTTCTCG SEQ ID NO 5 | |
| Tga3 P | HEX-AAGGAGTGAACGAAAGAAGTGGA-TAMRA SEQ ID NO 6 | 132 |

The following non limiting examples are provided to further illustrate the present invention.

EXPERIMENTAL PART

Example 1

Isolation and Growth *Trichoderma atroviride* SC1

The fungal strain *T. atroviride* SC1 was isolated in northern Italy from decayed hazelnut wood and obtained in pure culture by single spore method. It was maintained on potato dextrose agar (PDA; Oxoid, Cambridge, UK) slants at 4° C. in the SafeCrop Microorganism Collection (Istituto Agrario di San Michele all'Adige) and deposited in the CBS collection under the Budapest Treaty (CBS 122089). The strain was morphologically identified as *Trichoderma atroviride* P. Karst. and its identity was confirmed through ITS sequence analysis using the TrichOKEY identification tool, version 2.0 (www.isth.info).

*T. atroviride* SC1 is able to utilize a wide range of compounds as sole carbon and nitrogen sources. Fungal growth in media was significant superior when it was supplied with some nitrogen sources such Yeast Extract, Nitrite, Tryptone, Peptone, Glutamine and Asparagine or some carbon sources such Mannose, Galactose, Sucrose, Malt Extract, Cellobiose Glucose and Threalose.

Sorbitol, lactose, maltose fructose, arabinose xilose and $NH_4NO_3$, $KNO_3$, Serine, Arginine and glutamine did not promote mycelium growth.

The effects of the nitrogen sources (NS), $NR_4NO_3$, $NH_4Cl$, $KNO_3$, $NaNO_3$, $NaNO_2$, serine, arginine, glutamine, asparagine, tryptone and peptone (Sigma, St. Louis, Mo., USA), and carbon sources (CS), sorbitol, lactose, maltose, fructose, arabinose, xilose, threalose, glucose, cellobiose, malt extract, sucrose, galactose and mannose (Sigma), on *T. atroviride* SC1 mycelial dry weight were tested. NS and CS were filter-sterilized and added, at a rate of $2\cdot l^{-1}$ (NS) and $20\ g\cdot l^{-1}$ (CS), to autoclaved Czapek Dox Liquid media (Oxoid) amended with glucose (10 g·l$^{-1}$) (Sigma) or glycine (1 g·l$^{-1}$) (Sigma), when testing NS and CS, respectively. Flasks containing 100 ml of each nutrient media were each inoculated with an agar plug from a seven-day-old *T. atroviride* SC1 culture. After a 13-day incubation, the mycelia were harvested through filter paper and dried, and their dry weights were measured using a moisture balance AMB110 (Adam Equipment, UK). Five replicates were inoculated for each treatment and factor studied. The experiment was repeated twice.

Figure 1:
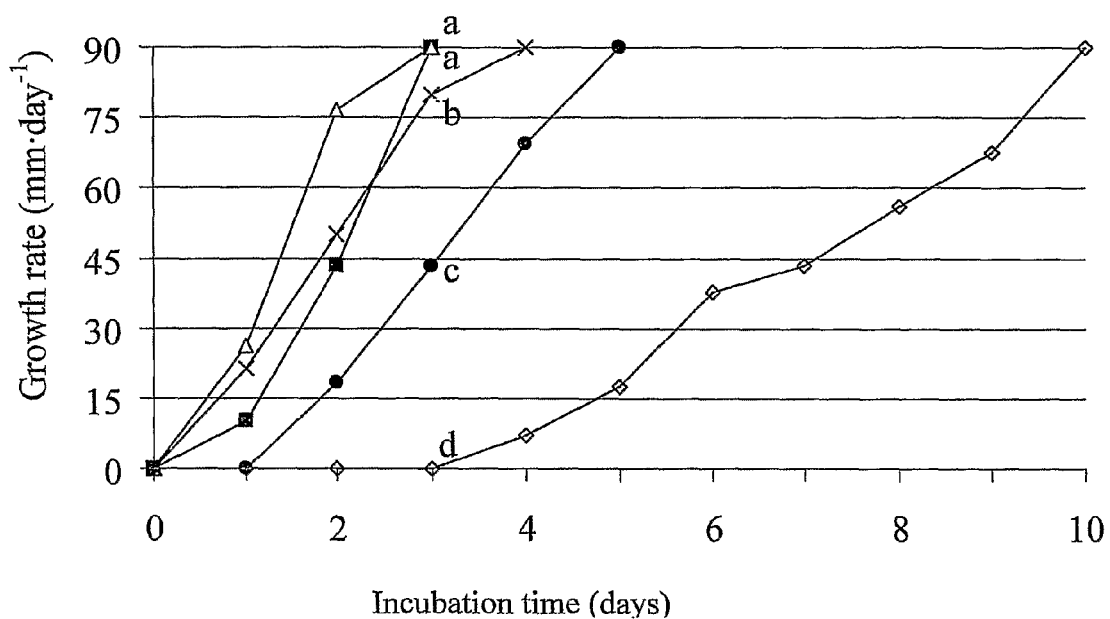
FIG. 1. Radial growth of *Trichoderma atroviride* SC1 at different temperatures. *Trichoderma atroviride* SC1 was grown on potato dextrose agar (PDA) and incubated at different temperatures: 10 (◇), 15 (●), 20 (■), 25 (△) and 30° C. (x). No growth was observed at −1, 5, 37 or 40° C. Data points are means of ten replicates. Values followed by the same letter are not significantly different (P≦0.05) according to Tukey's test. The period before the initiation of growth (lag period) was 1 day at 20, 25 and 30° C., 2 days at 15° C. and 3 days at 10° C.

*T. atroviride* SC1 was able to grow at temperatures between 10° C. and 30° C. The optimal temperature for growth was 25° C. At this temperature, the growth rate was significantly greater ($P \leq 0.05$) than at the other temperatures (FIG. 1). Therefore optimal growth was achieved at 25° C. The first conidia were produced on the third day after inoculation. Fungal radial growth at 20° C. was not significantly different than the growth observed at 25° C. *T. atroviride* SC1 did not grow at temperatures of 35° C. or higher. After thirty days of incubation at 35° C., the fungus was considered dead because it was not able to grow, even after the temperature was lowered to the optimal temperature of 25° C. Temperatures of −1 and 5° C. also inhibited mycelial growth. However, after 30 days at −1° C. and 5° C., the fungus was still able to grow when incubated again at 25° C. The lag phase, with little or no observable growth, was longest at 10° C. (2 days) and 15° C. (3 days).

Figure 2:
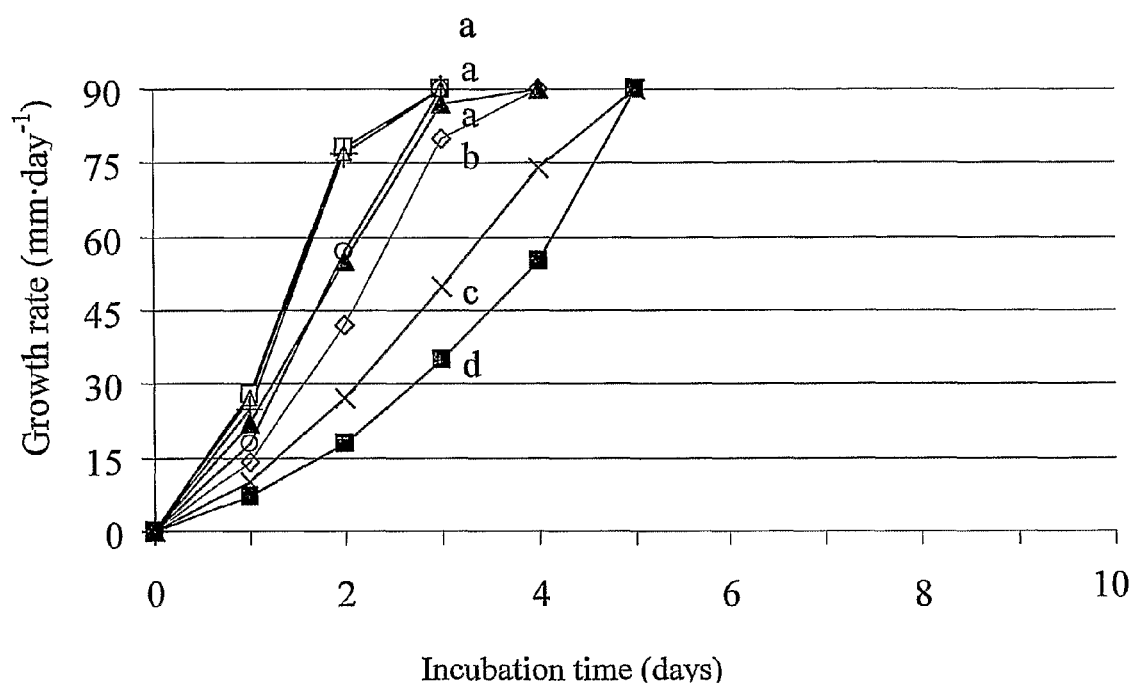
FIG. 2. Effect of pH *Trichoderma atroviride* SC1 radial growth. Growth was carried out on potato dextrose agar (PDA) at different pH levels. pH 3 (△), 4 (□), 5 (▲), 6 (+), 7 (●), 8 (◇), 9 (x) and 10 (■). Data points are means of ten replicates. Values followed by the same letter are not significantly different (P≦0.05) according to Tukey's test.

*T. atroviride* SC1 is tolerant of a wide range of pH levels (FIG. 2), with optimal growth observed on acidic media (pH 4-6). Mycelial growth of *T. atroviride* SC1 was significantly ($P \leq 0.05$) reduced on alkaline medium (pH $\geq 8$) and sporulation was reduced at pH 3, as well as pH values of 8 and above. The lag phase was the same (1 day) for all pH levels tested.

Figure 3:
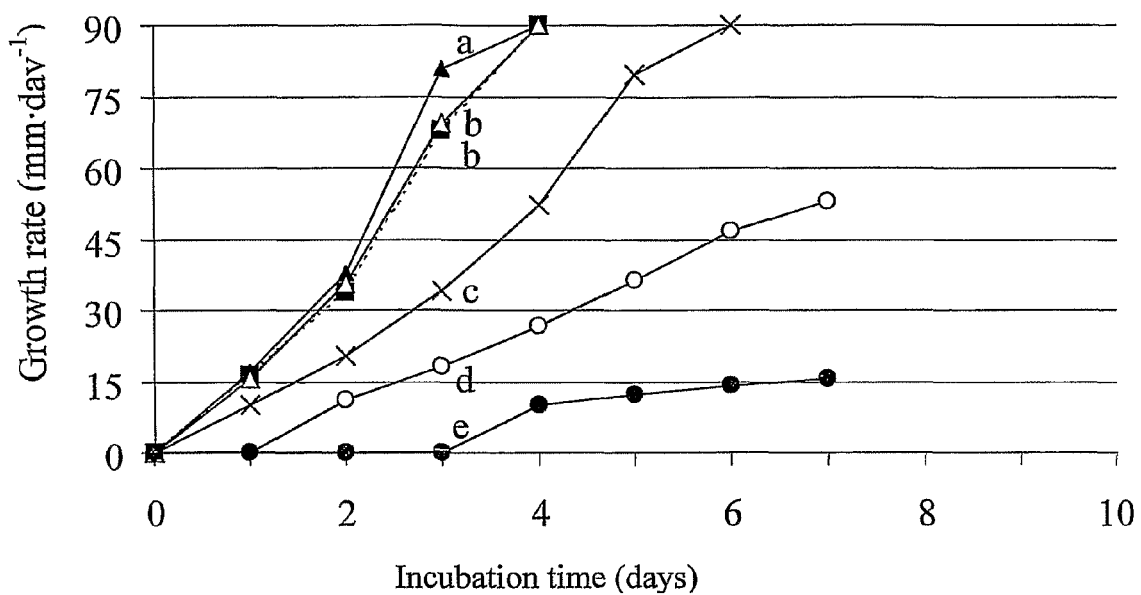
FIG. 3. Effect of water activity on the growth rate of *Trichoderma atroviride* SC1. *Trichoderma atroviride* SC1 was grown on potato dextrose agar modified with glycerol at the levels of water activity of 0.998 (▲), 0.990 (■), 0.980 (△), 0.960 (x), 0.940 (●) and 0.910 (○). Data points are means of ten replicates. Values followed by the same letter are not significantly different (P≦0.05) according to Tukey's test. The period before the initiation of growth (lag period) was 1 day at 0.998, 0.990 and 0.980, 2 days at 0.940 and 4 days at 0.910.

Growth rates were also influenced by changes in water activity ($a_w$) which is a measurement of the energy status of the water in a system, namely the vapor pressure of water divided by that of pure water at the same temperature (FIG. 3). The highest $a_w$ level tested (0.998) was the optimal level for fungal growth. When this parameter was decreased below 0.990, the growth rate was significantly reduced ($P \leq 0.05$) as compared to that for the unmodified PDA medium ($a_w=0.998$). Limited growth was observed at 0.910. The lag phase was longer when $a_w$ was decreased below 0.940 (2 days) and 0.910 (4 days).

Experimental Conditions

The effects of temperature, pH and water activity ($a_w$) on *T. atroviride* SC1 were tested in cultures grown on 90 mm Petri dishes containing PDA. Each plate was inoculated with one agar plug (5 mm diameter) collected from the margin of a seven-day-old culture. The inoculum plug was placed in the center of each plate. Mycelial growth was assessed daily. Ten replicate plates were inoculated for each level of the studied parameters.

In the temperature assay, the plates were incubated in the dark at −1, 5, 10, 15, 20, 25, 30, 37 and 40° C., with a medium pH of 5. In the pH assay, the pH levels of the media were adjusted to 3, 4, 5, 6, 7, 8, 9 and 10 after autoclaving by adding sterile solutions of 1 N HCl or 2 N NaOH. To test the effect of $a_w$, the media were modified by adding increasing amounts of glycerol to obtain $a_w$ levels of 0.990, 0.980, 0.960, 0.940 and 0.910. The pH of the media was adjusted to 4.5 with 1 N HCl or 2 N NaOH before autoclaving. The $a_w$ values of all the media were measured with an AquaLab series 3 instrument (Decagon, Pullman, Wash. USA). For the pH and $a_w$ assays, the plates were incubated in the dark at 25° C.

Radial growth was evaluated on the third day of incubation, which is approximately the time that the fungus needs to completely colonize a Petri dish of this size under optimal conditions.

Example 2

Detection and Quantification of *T. atroviride* SC1

Real-time PCR using the ech42 and tga3 primers resulted in amplification products from all DNA from *Trichoderma* spp. strains, other fungi and soil samples. The products gave a single melting peak for each gene, which indicates that the primers only amplified ech42 and tga3 products. Conversely, in the presence of the ech42 TaqMan probe containing the two SC1-specific point mutations of the ech42 gene sequence, only *T. atroviride* SC1 produced a single signal and no probe amplification product hybridization occurred for the other fungi (strain F122 and SB18 included), grapevine and soil samples, confirming the high specificity of the ech42 probe. An internal control (duplex reaction), consisting of the tga3 probe, confirmed the accuracy of the process by producing a signal in the real-time PCR examinations of all of the *Trichoderma* spp. samples.

Figure 4:
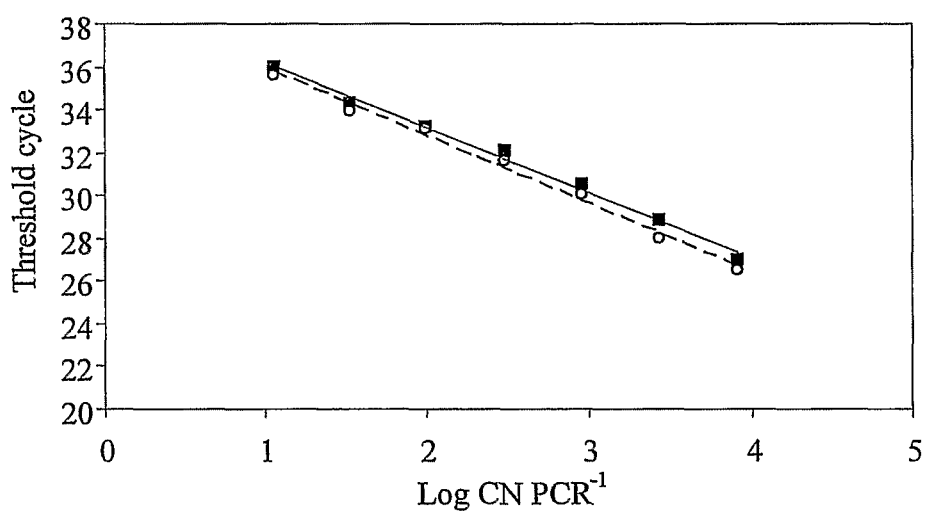
FIG. 4. ech42 and tga3 multiplex amplification. Amplification was carried out using the specific probe ech42 (■) and the general probe tga3 (○) of pure *Trichoderma atroviride* SC1 DNA. The two dilution curves overlap and have the same efficiency, coefficient of determination ($R^2$) and slope.

Duplex amplification of the ech42 and tga3 TaqMan probe for the series of concentrations of *T. atroviride* SC1 DNA occurred at the same threshold for each given concentration. This demonstrated that there is a single copy of the ech42 amplicon in the genome and a single copy of the Tga3 gene, and that these two sequences have similar standard curves. Our results also showed that the PCR reactions for each of these two sequences proceeded with similar levels of efficiency (FIG. 4).

This method yields an LOD of 5 genome copies per PCR reaction. For the soil samples, the calculated LOD increased to 35 copies per reaction mixture, equivalent to 6.2×10$^3$ conidia per g soil, and LOQ ranged from 2×10$^4$ to 3×10$^4$ g soil$^{-1}$, the latter delineated in the series of differentially inoculated soils (Table 2). The absolute LOD ranges from 8.5×10$^3$ to 1.2×10$^4$ copies per PCR reaction (Table 2).

Figure 5:
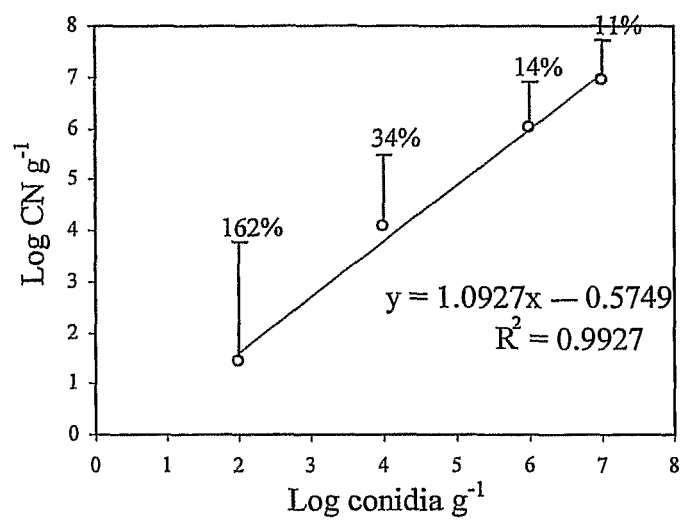
FIG. 5. Recovery of *Trichoderma atroviride* SC1 DNA by Real Time PCR. The nucleic acid quantity is expressed as number of haploid genome copies in one gram of soil inoculated with a known quantity of conidia. The standard deviation (%) was calculated from six independent quantifications.

The accuracy of the method is very high at the five tested conidial concentration levels (FIG. 5) resulting in the quantification of *T. artroviride* SC1 by the molecular method in quantities comprised from 10$^2$ to 10$^7$ conidia Experimental Conditions Real-time PCR primers and probe: *T. atroviride* SC1 endochitinase gene (ech42) (Carsolio et al., 1994) was amplified using consensus primers based on sequences already present in the NCBI GeneBank. The obtained complete sequence was compared and aligned with 34 sequences of the same database using the BLAST program (Altschul et al., 1997) and the ClustalW program (available at the European Bioinformatics Institute, European Molecular Biology Laboratory [http://www.ebi.ac.uk/clustalw/]), respectively. Several differences in nucleotide sequences were observed (in particular, two nucleotide mismatches in the first intron of a certain gene were noted) and only one sequence in the database (NCBI GenBank accession number AB041753.1 referring to *T. harzianum* SK-55 isolated in Japan) was identical to our isolate. Therefore, the real-time PCR primers and the strain-specific TaqMan probe set (Sigma Aldrich, St. Louis, Mo.) were designed based on these two nucleotide mismatches on the 3' strand of the ech42 gene, using the Primer Express v2.0 software (PE Applied Biosystems, Foster City, Calif.) (Table 1). A second primer set and TaqMan probe were designed for the tga3 gene, which encodes the G protein α subunit (Table 1).

Real-time PCR: Reactions were performed in 20 μl final volume containing: IQ Multiplex Power Mix buffer (Bio-Rad, Hercules, Calif.), 0.3 μM of each of the ech42 primers and the probe, 0.4 μM tga3 probe and 0.6 μM of each of the tga3 primers. The real-time PCR was run in a MJ Chromo4 thermocycler (MJ Research, Waltham, Mass.) using the following standard program: 2 min 30 s at 95° C. for initial denaturing, 40 cycles of 15 s at 95° C. and 1 min at 61° C. for an extension step in which the fluorescence signal was measured and analyzed by the Opticon2 software (MJ Research, Waltham, Mass.). When the samples were analyzed by SYBR Green I chemistry, the SYBR Green PCR Master Mix (Applied Biosystem, Foster City, Calif.) was used, along with 0.3 μM of the ech42 primer set and 0.3 μM of the tga3 primer set. The amplification conditions were then changed to: a 10 min hot start at 95° C., 40 cycles of 15 s at 95° C. and 1 min at 61° C. for extension, with a final melting curve from 40° to 90° C., during which the samples were slowly heated (0.5° C. every 10 sec).

The quantification of the DNA samples was done by interpolating the threshold cycle (Ct) values of the sample with the Ct values of a standard regression curve of known concentrations of purified genomic *T. atroviride* SC1 DNA previously quantified using the Qubit fluorimeter (Invitrogen Life Technologies, Carlsbad, Calif.). The standard curve was based on eight 1:3 serial dilutions of SC1 genomic DNA and included in each PCR run. The resulting curves had slopes ranging from 3.0 to 3.5, coefficients of determination higher than 0.9 and 100% PCR efficiency. The SC1 quantification was expressed as haploid copy number of the genome, considering that the *Trichoderma* single-copy genome size is 0.034

Specificity: The specificity of the method was tested on 50 isolates of *Trichoderma* spp. from culture collections (26 isolates from CBS, one from ATCC, 13 from University of Pavia and two from SafeCrop, namely F122 and SB18), two isolates used as commercial biofungicides (*T. harzianum* T39 and *T. harzianum* T22) and six *Trichoderma* isolates from soil collected in a commercial vineyard in northern Italy (GIS coordinates: N46° 10.897' and OE11° 06.983'). Seven of the examined isolates were identified as *T. atroviride*. Specificity was also tested on fungal genera commonly present in soils: *Aspergillus, Cladosporium, Penicillium, Fusarium, Aureobasidium, Mucor, Gliocladium, Rhizopus, Acremonium, Coelomycetes, Geotricum, Plasmopara* and *Armillaria* from the SafeCrop (21) or CBS (1) collections, or isolated (7) from soils.

All fungal isolates were grown on potato dextrose agar (PDA, Oxoid, Basingstoke, United Kingdom). DNA was extracted directly from 50-100 mg mycelia using the DNeasy plant Mini Kit (QIAGEN, Hilden, Germany). Specificity of the method for *T. atroviride* SC1 was tested by comparing the amplification products and melting curves obtained with the SYBR Green I tests with those obtained using the specific TaqMan probes for ech42 and tga3.

Ten soil samples, four from Trentino and six from other Italian regions (Marche, Valle d'Aosta, Emilia-Romagna and Calabria), were also included in the specificity test. DNA, if not otherwise noted, was always extracted from 200-mg soil samples dried overnight, according to the protocol prescribed for the PowerSoil DNA Isolation Kit (Mo Bio, Carlsbad, Calif.).

DNA from *Vitis vinifera* cv. Cabernet was included in the specificity test to control for amplification of DNA from root material present in *T. atroviride* SC1-treated soils. Plant DNA was extracted using the DNeasy Plant Mini Kit (QIAGEN, Italy). In the RT-PCR analysis of the genomic DNA of *T. atroviride* SC1, the other fungi and grapevine DNAs used as controls were loaded at approximately 0.2-1 ng, while 1-5 ng DNA (the total amount extracted from each 4-mg soil sample) was loaded in each PCR reaction.

Repeatability, precision and sensitivity: The repeatability of our real-time PCR procedure was estimated for a suspension of pure *T. atroviride* SC1 DNA and total DNA extracted from 7.5 g of soil previously inoculated with the fungus ($10^7$ conidia $g^{-1}$) and eluted in 4 ml, following the manufacturer's instructions for the PowerSoil Mega Prep DNA Isolation Kit (Mo Bio, Carlsbad, Calif.). The precision of the method was estimated using soils containing different concentrations of *T. atroviride* SC1. For this estimation, batches of 50 g of sieved, sterile sandy soil were mixed with 10-ml *T. atroviride* SC1 conidial suspensions to reach final concentrations of $10^7$, $10^6$, $10^4$ and $10^2$ conidia $g^{-1}$ soil. DNA was extracted from three independent samples for each concentration treatment, after the soils had been dried overnight at 60° C. (200 mg) and their respective conidial concentrations had been quantified in two independent real-time PCR runs.

The accuracy of the quantification method was calculated by comparing estimated genome copies with expected conidial concentration.

Sensitivity: The sensitivity of the real-time PCR method was defined by the limit of detection (LOD) and the limit of quantification (LOQ). LOD corresponds to the lowest copy number in the sample for which the standard deviation under repeatability conditions is 33% or lower. LOQ corresponds to the lowest copy number in the sample for which the standard deviation under repeatability conditions is 25% or lower. The absolute LOD of the method was calculated as the lowest number of copies that must be present in the sample to ensure at least 95% accuracy.

TABLE 1

Real-time PCR primers and probes designed for the detection and quantification of *Trichoderma atroviride* SC1.

| Primers and probes | Sequence (5'-3') | Amplified product (bp) |
|---|---|---|
| Endochitinase 42 gene (ech42) | | |
| Ech42 Fw | GTTCTGAGGCTGGAAGTTGC SEQ ID NO: 1 | |
| Ech42 Rv | ACGCCGTCTACTTCACCAAC SEQ ID NO: 2 | |
| Ech42 P | 6FAM-TACCCCTTCAATCACCAATTGTTAG-TAMRA SEQ ID NO: 3 | 112 |
| G protein a subunit gene (tga3) | | |
| Tga3 Fw | TGTTGAAGCATTGGGTTTGA SEQ ID NO: 4 | |
| Tga3 Rv | TGATTGAGGTGACGTTCTCG SEQ ID NO: 5 | |
| Tga3 P | HEX-AAGGAGTGAACGAAAGAAGTGGA-TAMRA SEQ ID NO: 6 | 132 |

The base mismatches in the ech42 TaqMan probe are in bold.

TABLE 2

The limit of detection (LOD) and limit of quantification (LOQ) determined using the relative standard deviation (RSDr) of the number of genome copies (CN) determined from two dilution series of pure *T. atroviride* SC1 DNA, two dilution series of total DNA extracted from a soil sample inoculated with $\log 10^7$ conidia g $soil^{-1}$ and analysis of the total DNA extracted from a series of soils inoculated with decreasing amounts of conidia.

| DNA | RSDr regression curve | | LOD-LOQ | | Absolute LOD | |
|---|---|---|---|---|---|---|
| | Equation | Coefficient of determination | CN $PCR^{-1}$ | CN g $soil^{-1}$ | CN $PCR^{-1}$ | CN g $soil^{-1}$ |
| SC1 1 | $Y = 0.4304x^{-0.1579}$ | 0.9874 | 5-31 | — | 8 | nd |
| SC1 2 | $Y = 0.369x^{-0.1359}$ | 0.9475 | 3-17 | — | 15 | nd |
| SC1 + soil 1 | $Y = 0.8811x^{-0.2696}$ | 0.9711 | 38-106 | $0.7 \times 10^4$-$1.9 \times 10^4$ | 60 | $1.1 \times 10^4$ |
| SC1 + soil 2 | $Y = 0.6821x^{-0.2089}$ | 0.9459 | 32-122 | $0.6 \times 10^4$-$2.2 \times 10^4$ | 35 | $0.6 \times 10^4$ |
| SC1 in soil series[z] | $Y = 313.01x^{-1.677}$ | 0.9929 | 26-130 | $0.7 \times 10^4$-$3.4 \times 10^4$ | 48 | $1.2 \times 10^4$ |

The LOD and LOQ were set at 33% and 25% of the relative standard deviation (RSDr), respectively. The absolute LOD corresponds to a DNA detection level of 95%.
[z]RSDr regression curve calculated based on four conidial concentrations.

Example 3

Methods for Production and for Treatment

*T. atroviride* SC1 was successfully grown on several common laboratory media as potato dextrose agar, nutrient broth, malt extract agar.

It was applied with one of the following three known methods: grown in culture broth, on rice or on barks/peat.

The three methods provided 99% of viable propagules of *T. atroviride* SC1.

*T. atroviride* SC1 produced on rice or grown on barks survives for at least one year at 15° C. at 98% RH. *T. atroviride* SC1 grown on vegetable amenders or barks Differences were observed with other *T. atroviride* strains, in particular *T. atroviride* F122 did not survive on barks or peat at the above mentioned conditions.

Experimental Conditions

Preparation of Agricultural Composition was Carried Out According to One of the Following Methods:

a) Inoculation with *T. atroviride* SC1 mycelium or conidia (at least $10^2$ conidia/L) of culture broth (nutrient broth or malt extract broth) and incubation under continuous shake, was carried out at a temperature between 20 to 25° C., for at least 48 h. The filtered or not filtered culture broth was sprayed to plants or incorporated to soil.

b) Sterilized boiled rice (or equivalent cereal) was inoculated with conidia *T. atroviride* SC1 mycelium or conidia (at least $10^2$ conidia/100 g) and incubated for 21 days at 25° C. For soil treatments rice—*T. atroviride* SC1 was mixed to soil to have an inoculum dose of $1 \times 10^6$ cfu $g^{-1}$ soil in the first 3 cm of soil. For foliar treatments *T. atroviride* SC1 conidia were collected from rice by washing with water and applied with or without the addition of other spray adjuvants (wetting agents, emulsifiers, etc.);

c) *T. atroviride* SC1 was grown on bark pieces preventively treated or not with a growth microbiological medium (nutrient broth) or nutrient substances containing carbon and nitrogen sources (grinded rice). Barks were inoculated with *T. atroviride* SC1 (at least $10^2$ conidia/100 g), incubated for at least two days or until colonization at 20-25° C. Inoculated barks can be used as amender in any time of the cultivation of plants providing control of existing soilborne pathogen or to prevent new infections. Vegetable amenders (peat) were inoculated without nutrient substances as done for barks.

Example 4

Survival of *T. atroviride* SC1 on the Strawberry Phylloplane

Figure 6:
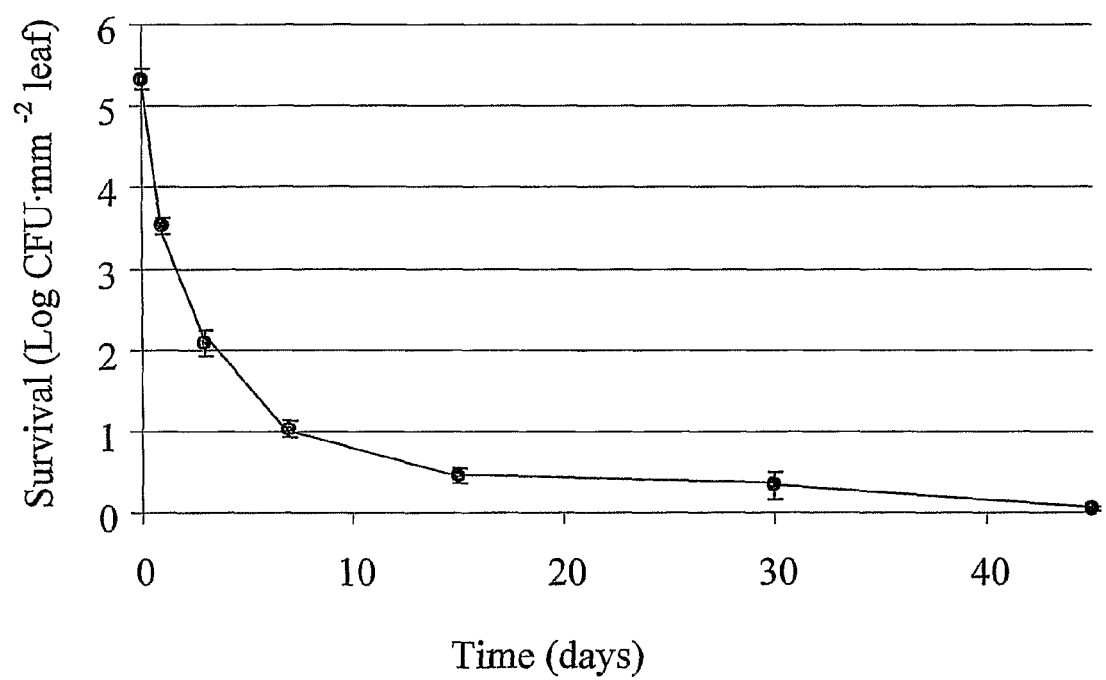
FIG. 6. Survival of *Trichoderma atroviride* SC1 on strawberry leaf evaluated as colony-forming units (CFU). Leaves were inoculated at day 0 by spraying a conidia-water suspension ($10^6$ CFU·ml$^{-1}$). Data points represent the averages of ten replicates. Data were transformed by log (x). Error bars represent the standard deviations of the means.

The population densities of viable *T. atroviride* SC1 conidia on the strawberry phylloplane decreased quickly during the first week after inoculation. The fungal population showed a continuous decline until the $15^{th}$ day after application, after which a low CFU concentration was maintained until the $45^{th}$ day when the experiment was concluded (FIG. 6). *T. atroviride* SC1 did not cause phytotoxicity neither is pathogenic to strawberry leaves, flowers or fruits and survived for more than one month on strawberry leaves.

Experimental Conditions

Conidial suspensions of *T. atroviride* SC1 were obtained by washing 21-day-old cultures grown on boiled rice with 0.01% Tween 80 (Sigma) in sterile distilled water (SDW). The conidial suspension was filtered through three layers of sterile lens tissue to remove mycelial fragments. The conidial concentration was determined using a Thomas haemocytometer and adjusted to a concentration of $10^6$ conidia·$ml^{-1}$. The concentration of viable conidia in the inoculum was determined by counting colony-forming units (CFUs) in a serial dilution on PDA amended with 2 ml·$l^{-1}$ Triton X-100 (Sigma). Colonies were counted following the incubation of the cultures at 25° C. for seven days.

Leaves of 10 strawberry plants kept under controlled greenhouse conditions (25±2° C., RH=60±10%) were uniformly sprayed with the *T. atroviride* SC1 inoculum using a hand sprayer. One randomly selected leaf was removed from each plant at 0, 1, 3, 7, 15, 30 and 45 days after inoculation. One leaf disc (25 mm diameter) was cut from each leaf using a sterile cork borer. Discs were transferred to Falcon tubes containing 5 ml of Tween 80 (0.01%), shaken for 4 min and then left to stand for 1 min. A dilution series in SDW was plated on a semi-selective media consisting of PDA amended with rose bengal (100 ppm), streptomycin (100 ppm) and chloramphenicol (50 ppm) to minimize the presence of bacteria. CFUs were counted on the appropriate dilutions and results were expressed as CFU·$mm^{-2}$ leaf. CFU counts from dilution plates were converted to CFU per $mm^{-2}$ of leaf. This experiment was performed twice and no significant experimental difference between the two experiments was observed.

Example 5

Survival of *T. atroviride* SC1 in Soil

Figure 7:
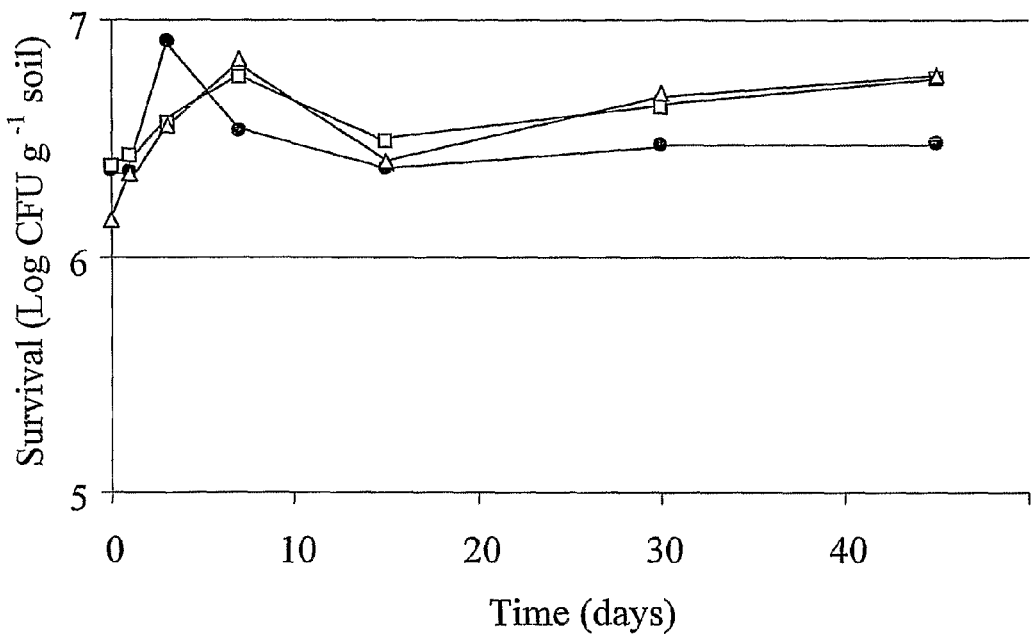
FIG. 7. Survival of *Trichoderma atroviride* SC1 in static soil microcosms. The fungus was applied at a rate of $10^6$ CFU·g$^{-1}$ soil at day 0 to three different sterile (a) and non-sterile (b) soils: Soil 1 (●), Soil 2 (□) and Soil 3 (△). Data points represent the averages of five replicates and were transformed by log (x). Different letters for each day indicate values that are significantly different (P≦0.05) according to Tukey's test.
Figure 7:
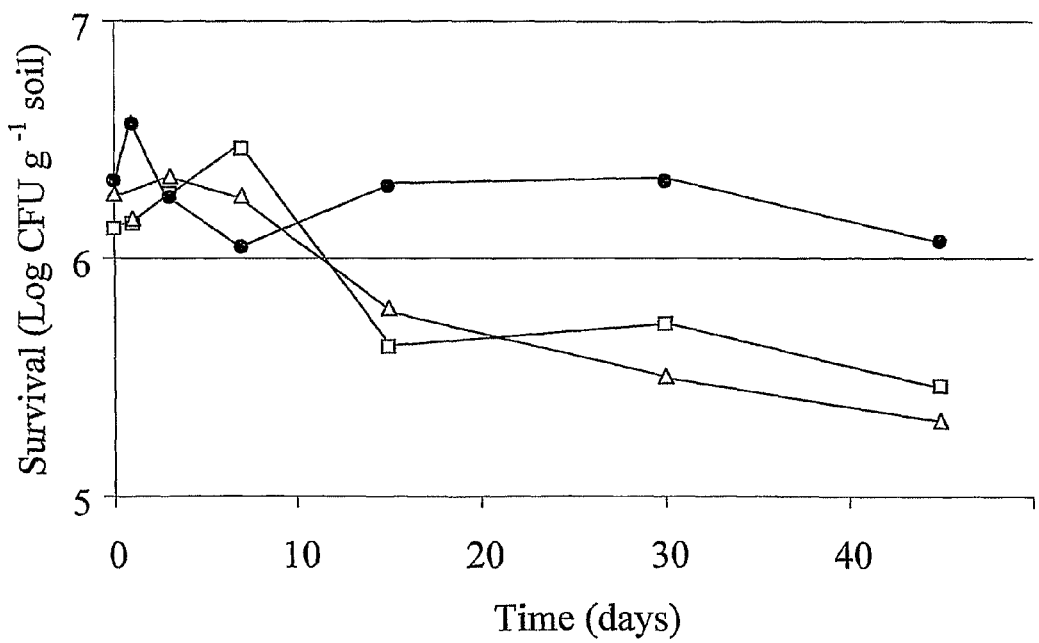

*T. atroviride* SC1 was able to survive in at least three different types of soils. After its introduction into the soils, *T. atroviride* SC1 survived until the end of the experiment (45 days), as indicated by its recovery on dilution plates from the sterile and non-sterile soils as shown on FIG. 7. The different soil characteristics also influenced fungal survival. The results obtained for the sandy loam soils (2 and 3) with high levels of organic matter were similar to one another, but different from the results obtained for the clay loam (Soil 1), which also had less organic matter.

Soil sterilization by autoclaving was associated with longer survival of *T. atroviride* SC1. In the sterile soils, the fungal concentration increased by almost one order of magnitude in the third day, reaching a maximal concentration of $10^7$ $CFU \cdot g^{-1}$ dry soil in sterile Soil 1, and a little less in Soils 2 and 3. After that, the *T. atroviride* concentration stayed between $10^6$ and $10^7$ $CFU \cdot g^{-1}$ dry soil until 45 days after inoculation (FIG. 7a) in all soil types. The final fungal concentrations in the sterilized soil were significantly higher ($P \leq 0.05$) for Soils 2 and 3 than for Soil 1.

There were significant differences between the CFU values for the sterile and non-sterile treatments for each soil type at each evaluation date, except for Soil 1 at 30 days after inoculation. *T. atroviride* SC1 CFU values increased in sterilized soil. The CFU values in non-sterile Soil 2 were similar to those of non-sterile Soil 3. In untreated Soil 1, there was a small increase in the number of CFUs at one day after inoculation, but the conidial concentration at the end of the experiment in all soil types was lower than that of the initial inoculum. The final conidial (CFU) concentration in untreated soils was significantly higher ($P \leq 0.05$) for Soil 1 than Soils 2 and 3. The effect of soil sterilization on the survival of *T. atroviride* SC1 was more pronounced in Soils 2 and 3 than in Soil 1.

In the untreated (non-inoculated) microcosms used as a control, a very low level of native *Trichoderma* spp. (1 to $3 \cdot 10^2$ CFU $g^{-1}$) was detected, but none of the CFUs were identified as *T. atroviride*.

Experimental Conditions

The soil survival assay was based on the method described by Bennett et al. (2003), with some modifications. Three soil types from northern Italy (Trentino region) with different physical and chemical characteristics (Table 1) were used. Soil was dried at room temperature and sieved (mesh<2 mm). Sieved soil (100 g) was placed in 500 ml polypropylene bottles and samples were left untreated (non-sterile) at room temperature or autoclaved (121° C. for 30 min) twice on consecutive days (sterile).

The inoculum was prepared as describe above. The experiment was performed under sterile conditions. Conidia were added to the soil to get a final concentration of $10^6$ conidia $\cdot g^{-1}$ soil and mixed with a sterile spatula. The bottles were incubated at room temperature. Five replicates were set up for each soil type X soil treatment (non-sterile and sterile) combination.

A subsample of soil (1 g) was removed aseptically from each sample bottle using a sterile sample-spoon (PBI International, Whitstable, UK) and placed in 10 ml 0.01% Tween 80, shaken for 4 min and left to stand for 1 min. A dilution series was set up and plated on the semi-selective media as described above. CFUs were counted on the appropriate dilution plates after seven days of incubation at 25° C. and expressed as $CFU \cdot g^{-1}$ dry soil. CFU assessments in the soil samples were carried out immediately after inoculation and at 1, 5, 10, 20, 30, and 45 days after inoculation. CFU counts from dilution plates were expressed as CFU per gram of dry soil ($CFU \cdot g^{-1}$).

Example 6

Survival of *T. atroviride* SC1 in a Vineyard Soil

The survival in soil was also checked in a commercial vineyard during an entire year. The experiment was repeated twice.

*T. atroviride* SC1 was able to survive at high conidia concentration ($10^8$ CFU·g dry soil$^{-1}$) on the first layer of soil (soil surface) for a long time (at least 18 weeks after treatment) in both years. *T. atroviride* SC1 vertically migrates in the soil very quickly after the treatment (one week) reaching a depth of 0.4 m. Then CFU concentration maintained stable values during two years until assessment on the $18^{th}$ week. A gradient in population densities was present in both years from the surface to the depth soil layers. The highest number of CFU detected was $10^5$ CFU g dry soil$^{-1}$ at 0.1 m of soil depth, about $10^4$ at 0.2 m and $10^2$ CFU g dry soil$^{-1}$ at 0.3 and 0.4 m. Differences in population dynamics between the two years were present only in the CFU concentration in the soil surface five and nine weeks after treatment significantly different (Tukey's test; $\alpha$=0.05). In particular after 9 weeks *T. atroviride* SC1 CFU on soil surface increased even more than the initial inoculum concentration ($10^9$ CFU g dry soil$^{-1}$), after an initial decrease on the $5^{th}$ week. One year after soil inoculation *T. atroviride* SC1 was detected at a concentration of $10^2$-$10^3$ CFU g dry soil$^{-1}$ for both experiments at concentration comparable to indigenous *Trichoderma* spp. on untreated area. Real Time PCR method confirmed the absence of the strain before its soil introduction and the persistence of the strain in the soil layers.

The linear relationship (y=0.8472x+0.1105, R2=0.6794) between the results obtained with the two methods (CFU counting and molecular method) confirms the efficiency of the molecular detection of *T. atroviride* SC1.

After 9 weeks of its release in the soil, *T. atroviride* SC1 was found at a distance of 0.5 and 2 m from the treated holes in the soil surface, at 0.1 m and 0.3 m of soil depth. The CFU was significantly higher (Tukey's test; $\alpha$=0.05) than the indigenous *Trichoderma* spp. population isolated in the untreated area, in the soil surface, at 0.5 and 2 m from the treated holes and at 10 cm of soil depth at 0.5 m of distance from the treated holes. The SC1 conidia concentration in the others soil layers at 0.5 and 2 m of distance from the treated holes was not significantly higher (Tukey's test; $\alpha$=0.05) than the indigenous *Trichoderma* spp. population isolated in the untreated area. Frequency of occurrence of *T. atroviride* SC1 was high (respectively 100% at 0.5 m from the treated holes at all soil depth) and decreased to 90, 70 and 30% at 2 m of distance from the treated holes respectively in soil surface, at 0.1 and 0.3 m of soil depth.

Eighteen weeks after its introduction in the soil, it was still possible to recover *T. atroviride* SC1 in the soil surface both at 2 and 4 m of distance from the treated holes. These CFU concentrations were not significantly different (Tukey's test; $\alpha$=0.05) compared to conidial concentration of indigenous *Trichoderma* spp. obtained from the untreated area. Even if low concentrations were detected after 18 weeks, the frequency of occurrence of *T. atroviride* SC1 was high (respectively 80 and 70% at 2 and 4 m from the treated holes).

*T. atroviride* SC1 was found on leaves of vines planted in the treated soil. The number of *T. atroviride* SC1 CFU mm$^2$ of leaf$^{-1}$ was significantly higher (Tukey's test; α=0.05) on the leaves of plants in treated soil than indigenous *Trichoderma* spp. isolated on the plants in the untreated areas. There was significant difference (Tukey's test; α=0.05) in *T. atroviride* SC1 CFU per surface unit (mm$^2$) between top and bottom leaves of plants in treated areas Eighteen weeks after planting in the treated holes the concentration of *T. atroviride* SC1 in the grapevine rhizosphere was 10$^7$ CFU g dry soil.

Numbers of leaves, numbers of shoots, dry root weight, stem length and total length of the grapevine plants, do not demonstrated significantly differences between grapevines planted in soil untreated or treated with *T. atroviride* SC1 (Tukey's test; α=0.05, data not shown), indicating that the fungus is nor pathogenic to grapevine culture.

The isolation of *T. atroviride* SC1 one year after inoculation indicates that it can tolerate low winter temperatures and humidity fluctuations in the soil. The concentration of *T. atroviride* SC1 in the soil one year after inoculation similar to indigenous *Trichoderma* spp. indicates that it can establish in the soil.

Same tests were carried out in 2006 with a different strain, *T. atroviride* F122. This strain was detected only until 18 weeks after inoculation and was not detected one year after inoculation. The inability of surviving of *T. atroviride* F122 in comparable growth conditions one year after inoculations demonstrate the superiority of *T. atroviride* SC1 to other strains.

Experimental Conditions

In all experiments, the concentration of viable *T. atroviride* SC1 was estimated by collecting 1 g samples of soil from each plot, placing each sample in 10 ml of sterile water and then plating 1 ml of this suspension, after 10-fold serial dilutions, on semi-selective media. Fungal colonies were counted after seven days of incubation and the population numbers were presented in terms of log CFU g dry soil$^{-1}$. The soil dry weight was estimated after the incubation of the sample (or sub-sample) at 60° C. for 48 h. The conidia on the rice used as inoculum always had an average viability close to 100%. *T. atroviride* SC1 colonies were distinguished from other *Trichoderma* species by their characteristic aerial mycelia (white at first, then rapidly turning yellowish green to olive green). For the unequivocal identification of our isolate, the identity of almost 10% of the colonies from each plate that had been morphologically identified as *T. atroviride* was confirmed by PCR analysis using primers and a Taq-Man probe set based on a base mutation of the endochitinase gene (Ech42) that is specific for *T. atroviride* SC1 (as in example 2). Experiments consisted of six plots of 0.6×0.6 m each, which were located between grapevine plants in the row in the vineyard. Three plots were inoculated with *T. atroviride* SC1 and each received 500 g of the boiled-rice medium with the fungus grown on it. The inoculum was mixed into the soil surface layer (approximately 30 mm deep). The initial concentration of the fungal inoculum in this layer was estimated to be 10$^8$ CFU g dry soil$^{-1}$. Three additional uninoculated plots were used as an untreated control. In each plot, the soil was sampled by excavating the external part of one side of the plot and exposing the soil profile. Sampling was done by collecting three transverse carrots of soil (50 ml, 300 mm in diameter) at different depths (on the surface and at 0.1, 0.2, 0.3 and 0.4 m) and time points (at inoculation time and 1, 5, 9 and 18 weeks after *T. atroviride* SC1 inoculation). An additional soil sampling was made one year after the inoculation of the first experiment.

A sub-sample of soil (1 g) was removed from each sample using a sterile spoon. The sub-sample of soil was placed in 10 ml 0.01% Tween 80 (Acros Organics, Geel, Belgium), shaken for 4 min using a vortex (Heidolph Instruments, Schwabach, Germany) and left to stand for 1 min. A dilution series in sterile distilled water were set up and the diluted suspensions were plated on Petri dishes containing the semi-selective media. These Petri dishes were then incubated at 25° C. and final colony counts were made on the cultures corresponding to the appropriate dilutions (CFU within the range of 30-300 colonies per plate) after five days of incubation. There were three replicates for each soil sample. Results were expressed as CFU g dry soil$^{-1}$. The identities of *T. atroviride* SC1 colonies were confirmed as described in example number.

Real-time PCR were used to determine the numbers of *T. atroviride* SC1 genome copies (CN) in all samples of 2006. For the RT-PCR analysis, two independent sub-samples were collected for each combination of depth and time and the DNA extraction and real-time PCR analysis of each sample was performed as described in example 2.

The dispersion of *T. atroviride* SC1 conidia was examined in 2006. Holes measuring 0.3×0.3×0.3 m were dug in the vineyard row between grapevine plants. Ten holes were filled up with a mixture of the dug soil and *T. atroviride* inoculum (400 g hole$^{-1}$). The initial fungal inoculum concentration was 10$^6$ CFU g dry soil$^{-1}$. The other ten holes were filled back in with the untreated dug soil. A one-year-old grapevine plant (Pinot gris on Kober 5BB) was planted in each hole.

Two sets of soil samples were collected. The first sampling was carried out nine weeks after inoculation in both the treated and untreated holes (0 m) and at horizontal distances of 0.5 and 2.0 m from the hole. At each of these distances, soil samples were collected at three soil depths (0, 0.1 and 0.3 m). A second sampling was performed 18 weeks after inoculation and, at that time, soil samples were collected only on the surface (first 30 mm of soil) of the holes and at horizontal distances of 2.0 and 4.0 m from the inoculation sites. Samples were collected and the number of CFU in each sample was determined as previously described. Dispersion was evaluated in terms of *T. atroviride* SC1 concentration (CFU g dry soil$^{-1}$) and frequency (percentage of soil samples with at least one CFU).

The migration of *T. atroviride* SC1 from the soil to the leaves of the grapevines was evaluated 10 weeks after soil inoculation. Three apical leaves and three bottom leaves were removed from each plant (each plant had an average of 15 leaves) growing in the treated and untreated holes. Each freshly harvested leaf was transferred to a Falcon tube containing 30 ml of sterile distilled water plus 0.01% Tween 80. These tubes were shaken for 3 minutes and 1 ml of each of the resulting suspensions was then transferred to a Petri dish containing the semi-selective media. CFU were counted following seven days of incubation at 25° C. Leaf area was calculated using an image processing and analysis program, Image Tool version 2.0 (UTHSCSA, San Antonio, Tex., USA). At the end of the experiment, plants were removed from the soil. Soil that did not tightly adhere to roots was carefully removed with light shaking and the roots were then shaken vigorously in a plastic bag to dislodge the rhizosphere soil. Sampling of the rhizosphere soil and CFU counting for these samples (sub-samples of 1 g; three replicates) was done as previously described.

To evaluate the influence of *T. atroviride* SC1 on plant growth, measurements of total length, stem length and the numbers of leaves and shoots were taken for each plant in the treated and untreated areas in the ninth and 18$^{th}$ weeks after soil inoculation. The root dry weight was also determined for each plant at the end of the experiment (18$^{th}$ week after inoculation).

Example 7

Biocontrol Activity In Vitro

In the dual culture bioassay, *T. atroviride* SC1 inhibited completely *B. cinerea* and *A. mellea* with an antagonistic efficacy of 100%.

Experimental Conditions

In vitro *T. atroviride* SC1 antagonism to one foliar and fruit (*Botrytis cinerea*) and one soilborne (*Armillaria mellea*) pathogen were tested using the dual culture method as follows: the pathogens (*B. cinerea* or *A. mellea*) were inoculated at distance of 2 cm (A) from *T. atroviride* SC1 (B) on PDA of Petri dishes (90 mm diameter). *B. cinerea, A. mellea* and *T. atroviride* SC1 were each grown alone as untreated controls. There were at least three replicates of each combination. Antagonistic efficacy was calculated after one week of incubation at 20° C., as (AD-AC)×100/AD, where AC and AD are the radial growth of the pathogen with and without *T. atroviride* SC1, respectively.

Example 8

Biocontrol of Powdery Mildews

*T. atroviride* SC1 controls powdery mildew (*Podosphaera xanthii*) on horticultural crops as cucumber and zucchini at the same level of Sulphur which is one of the most widely chemical fungicides used and which was therefore included as standard (FIG. 8). In particular it is observed that *T. atroviride* SC1 controls the disease at the same level as sulphur and better than the two *Trichoderma* strains used as standards. Also on zucchini the biocontrol efficacy was present (significant difference with untreated).

Experimental Conditions

Plants with at least five well expanded leaves of susceptible cultivars were used. The cultivars used were Afrodite or Xara for zucchini and 807 for cucumber. Seeds were planted in peat: volcanic gravel potting mix (1:1) in one liter pots and grown in a CPM-free greenhouses kept at 20-30° C. with a natural photoperiod. There were five to six replicates (pots) of each treatment and crop. *P. xanthii* inoculum was initially collected in commercial greenhouses on naturally infected zucchini and cucumber plants and later kept on cucumber and zucchini plants by infecting 3 weeks old plants and maintaining the infected plants for up to one month in a separate greenhouse compartment. Conidia were obtained by washing with water leaves bearing fresh and new conidiating mycelium and immediately sprayed onto plants. Inoculum concentration was approx. $10^7$ conidia $ml^{-1}$ and a volume of 5 ml $plant^{-1}$ was applied. Once dry, plants were incubated overnight at 22° C. and high relative humidity (RH>95%). After artificial inoculation day-time conditions were 20-30° C., with 30-70% RH and night-time conditions were 15-20° C. with 85-90% RH. Plants were arranged in completely randomized blocks.

*T. atroviride* SC1 was grown in nutrient broth (method a), example 3) and sprayed with a hand sprayer on leaves. An untreated control, sulphur (Thiovit, Syngenta Crop Protection) and a commercial biocontrol agent (*Trichoderma harzianum* T39, Trichodex®), Intrachem bio) were also included in the experiment. For each treatment 5 ml of solution $plant^{-1}$ was sprayed for plant. Experiments were repeated at least twice. *T. atroviride* SC1 and control were arranged in a fully randomized block. Beginning seven days after inoculation, leaves were checked weekly for powdery mildew symptoms. When present, disease severity was scored. Disease severity was measured as the percentage of symptomatic leaf area on all leaves.

Analysis of variance (ANOVA) was used to analyze arcsin transformed and normalized data. This analysis was performed using Statistica, version 7 (StatSoft, Tulsa, Okla., USA). Means were separated according to Tukey's HSD test ($\alpha$=0.05). Kursal-Wallis non parametric test was used when conditions for the ANOVA were not fulfilled.

Example 9

Biocontrol of Agents of Wood Diseases (Esca Disease)

Figure 9:
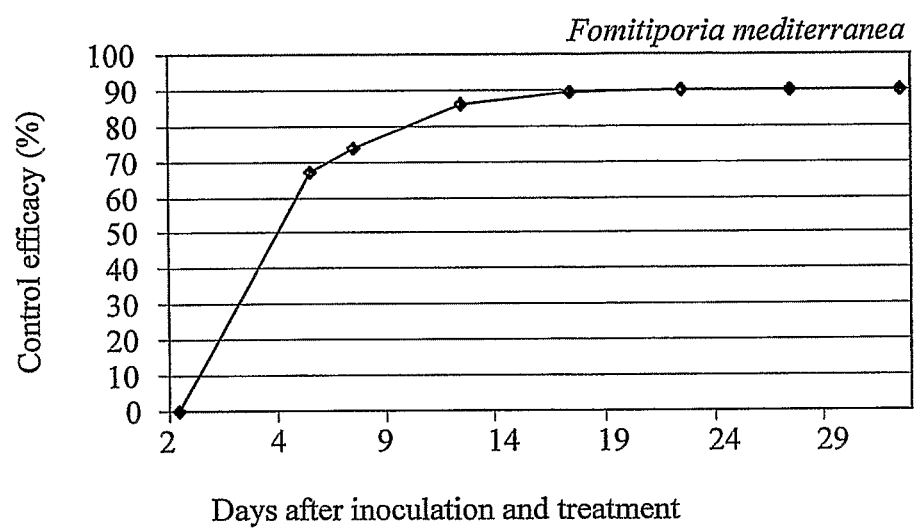
FIG. 9. Efficacy of *Trichoderma atroviride* SC1 on growth of the three major causal agent of Esca Disease. (*Phaeomoniella chlamydospora*: panel A; *Phaeoacremonium aleophilum*, panel B; *Fomitiporia mediterranea*, panel C). The control efficacy was calculated according the formula: [(C−T)/C]×100, where C is the growth of the pathogen without the treatment and T is the growth with the *Trichoderma atroviride* SC1 treatment. The inoculation of Esca causal agents and *T.*

*T. atroviride* SC1 controls the three main pathogens of Esca disease. The efficacy of control of *Phaeomoniella chlamydospora, Phaeoacremonium aleophilum* and *Fomitiporia mediterranea* is very high and close to 100% (FIG. 9). The graphs represent the average of five replicates (Petri dishes). The control efficacy of *T. atroviride* SC1 was always better than the biocontrol agent used as standard (*Bacillus subtilis* F77).

Experimental Conditions

Each of the three pathogens mentioned above was inoculated on PDA in Petri dishes 3 cm from the border and incubated for one week at 25° C. Then *T. atroviride* SC1 was inoculated on the opposite site, at a distance of 3 cm form the border. Five replicates were done for each pathogen and for the untreated control.

The mycelium growth was measured 2, 4, 9, 14, 19, 24 and 29 days after treatment, in particular C is the growth in the untreated (mm) and T the growth on the treated with *T. atroviride* SC1 (mm). The efficacy was calculated with the following formula [(C−T)/C]×100 (Sivakumar et al., 2000).

Example 10

Biocontrol of Root Rots

*Armillaria mellea* and *A. gallica* are the major causal agent of root roots on several crops. *T. atroviride* SC1 is effective against these two pathogens and is also more effective *T. harzianum* T39 as a standard biocontrol agent. It reduced the growth of the pathogens and eventually killed them. This is evident in controlled conditions experiment against the two pathogens grown on wood pieces shown on FIG. 10, where myceliar growth of *Armillaria mellea* and *Armillaria gallica* (root rot causal agents) in presence of *Trichoderma atroviride* SC1 or in its absence have been compared. The experimental effect of *Trichoderma harzianum* T39—commercial name Trichodex®—is shown here for comparison. The growth is expressed as average of diameter of five replicates grown on wood pieces on PDA on Petri dishes at 20° C.

*T. atroviride* SC1 is also able to prevent infections on plants. In fact, the percentage of dead (infected) plants was assessed after 6 months from the first application, which is when the diseases symptoms become visible and it was found that *T. atroviride* SC1 protected strawberry plants from *A. mellea* (60% of protection) and *A. gallica* (100% of protection). Conversely *T. atroviride* F122 gave only 20% of protection and *T. harzianum* T39 only 13% against the disease (values on FIGS. 10 and 11 are percentages calculated on 10 replicate plants).

In the case of strawberry plants it significantly reduced the disease caused by *A. mellea* and *A. gallica* even after 6 months from the application.

*T. atroviride* F122 was used as comparison for *A. mellea* (FIG. 11) and it was found to display a significantly lower activity than the SC1 strain.

Experimental Conditions

*A. mellea* and *A. gallica* were inoculated on wood pieces placed on PDA in Petri dishes on one side of the wood piece and incubated for one week at 25° C. Then *T. atroviride* SC1 was inoculated on the opposite site. Five replicates were done for each pathogen and for the untreated control. The mycelium growth was measured weekly after the treatment for 6 weeks.

Strawberry plants (Elsanta cv) were inoculated by putting three infected wood pieces with *A. mellea* or *A. gallica* close to the crown of the plants. Plants were treated with *T. atroviride* SC1 grown with method b) (see Example 3) and method c) as described in Example 3, was alternatively used for the same purpose for protecting those plants that need high levels of organic matter as blueberry plants giving the same results obtained with strawberry plants shown in FIG. 11. Plants were kept under greenhouse controlled conditions.

REFERENCES

Altschul S F, Madden T L., Shaffer A A, Zhang J, Zhang Z, Miller W, Lipman D J. 1997 Gapped BLAST and PSI-BLAST: a new generation of protein database search programs. Nucleic Acid Res. 25:3389-3402.

Bennett A J, Leifert C, Whipps J M. 2003 Survival of the biocontrol agents *Coniothyrium minitans* and *Bacillus subtilis* MBI 600 introduced into pasteurised, sterilised and non-sterile soils. Soil Biol Biochem; 35: 1565-1573

Carsolio C, Gutierrez A, Jimenez B, Van Montagu M, Herrera-Estrella A. 1994. Characterization of ech-42, a *Trichoderma harzianum* endochitinase gene expressed during mycoparasitism. PNAS USA; 91:10903-10907.

Elad Y. *Trichoderma harzianum* T39 preparation for biocontrol of plant disease-control of *Botrytis cinerea, Sclerotinia sclerotiorum* and *Cladosporium flavum*. Biocontrol Sci Techn 2000; 10: 499-507.

Harman G E. Myths and dogmas of biocontrol: changes in perceptions derived from research on *Trichoderma harzianum* T-22. Plant Dis 2000; 84(4): 377-393.

Klein D, Eveleingh E. 1998 Ecology of *Trichoderma*. In: Harman G E, Kubicek C P, eds. *Trichoderma & Gliocladium*, vol. 1. Taylor & Francis, Padstow, UK: 57-74.

Kredics L, Anthal Z, Manczinger L. 2000 Influence of water potential on growth, enzyme secretion and in vitro enzyme activities of *Trichoderma harzianum* at different temperatures. Curr Microbiol; 40: 310-314.

Kredics L, Manczinger L, Anthal Z, Pénzes Z, Szekeres A, Kevei F, Nagy E. 2004 In vitro activity and pH dependence of mycelial growth and extracellular enzyme activities of *Trichoderma* strains with biocontrol potential. J Appl Microbiol; 96: 491-498.

Longa C. 2007 Fungal biocontrol agents: identification and fate of *Trichoderma atroviride* P. Karst. in the environment. PhD thesis.

Paulitz T C. 2000 Population dynamics of biocontrol agents and pathogens in soil and rhizospheres. Eur J Plant Pathol; 106: 401-413.

Sivakumar D, Wilson Wijeratnam R S, Wijesundera, R L C, Marikar F M T, Abeyesekere M. 2000 Antagonistic effect of *Trichoderma harzianum* on postharvest pathogens of rambutan (Nephelium lappaceum). Phytoparasitica; 28: (3), pp. 240-247.

Spencer D M 1978 The Powdery Mildews. Academic Press, New York, USA.

The invention claimed is:

1. An isolated culture of *Trichoderma atroviride* SC1, CBS n° 122089, as a biocontrol agent.

2. A method of treating plant fungal diseases in a plant comprising administering to said plant the isolated culture of *Trichoderma atroviride* SC1 according to claim 1.

3. An agricultural composition comprising the isolated culture of *Trichoderma atroviride* SC1 according to claim 1 as the active principle.

4. The composition according to claim 3 wherein the composition comprises an effective amount of $10^2$-$10^3$ *Trichoderma atroviride* SC1 conidia $mL^{-1}$ or $g^{-1}$.

5. The composition according to claim 3 further comprising a second biocontrol agent and/or an additive, an emulsifier, a plant nutrient, a wetting-agent, a plant micro-nutrient or a substratum.

6. The composition according to claim 5 wherein the substratum is selected from the group consisting of: a nutrient culture medium, a cereal or a derivative thereof, an amendant, a vegetable or a part thereof, peat, wood or a piece thereof, clay or barks.

7. A method for preparing the agricultural composition according to claim 3 comprising inoculating an isolated *Trichoderma atroviride* SC1, CBS n° 122089 strain into or onto a substratum and allowing it to grow at a temperature from 1 to 30° C. until obtaining a number of *Trichoderma atroviride* SC1 conidia of at least $10^2$-$10^3$ $ml^{-1}$ or $g^{-1}$.

8. The method for preparing an agricultural composition according to claim 7 further comprising a lyophilization step following the step of allowing it to grow.

9. The method according to claim 7 wherein said substratum is selected from the group consisting of: a nutrient culture medium, a cereal; or a derivative thereof, a vegetable or a part thereof, wood or a piece thereof, an amendant, peat, clay, or bark.

10. The method according to claim 9 wherein said nutrient culture medium comprises at least a carbon and a nitrogen source.

11. The method according to claim 10 wherein said carbon source is selected from the group consisting of Mannose, Galactose, Sucrose, Malt Extract, Cellobiose Glucose and Threalose.

12. The method according to claim 10 wherein said nitrogen source is selected from the group consisting of: Yeast Extract, Nitrite, Tryptone, Peptone, Glutamine and Asparagine.

13. The method according to claim 9, wherein said cereal is rice or wheat.

14. The method according to claim 9, wherein said substratum is treated with a nutrient culture medium before inoculum of the *Trichoderma atroviride* SC1.

15. The method according to claim 14 wherein said nutrient culture medium is sprayed on the substratum.

16. The method according to claim 15 wherein said substratum is bark.

17. A method of protecting a plant from disease caused by a plant pathogenic fungus characterized by treating at least a part of the plant or soil within the proximity of said plant with the composition according to claim 3.

18. The method of claim 17 wherein said part of a plant is a leaf, a fruit, a seed, and a wound.

19. The method of claim 17 wherein the agricultural composition is prepared by inoculating an isolated *Trichoderma atroviride* SC1, CBS n° 122089 strain into or onto a substratum and allowing it to grow at a temperature of 1 to 30° C. until obtaining a number of *Trichoderma atroviride* SC1 conidia of at least $10^2$-$10^3$ ml$^{-1}$ or g$^{-1}$.

20. The method according to claim 17 wherein said pathogenic fungus is selected from the group consisting of those causing wood diseases (*Phaeomoniella chlamydospora, Phaeoacremonium aleophilum* and *Fomitiporia mediterranea*), foliar disease (the powdery mildew causative agent *Podosphaera xanthii*), fruit and flower diseases (*Botrytis cinerea*) and root diseases caused by *Armillaria* genus (*Armillaria mellea* and *A. gallica*).

21. The method according to claim 20 wherein said plant is selected from the group consisting of: Cucurbitaceae, Rosaceae, Vitaceae, Crucifereae, Compositae, Ubelliferae, Solanaceae and Liliaceae.

22. The method according to claim 21 wherein said plant is selected in the group consisting of: Cucurbitaceae, Rosaceae or Vitaceae.

23. An isolated culture lyophilizate or an isolated culture in agar of *Trichoderma atroviride* SC1, CBS n° 122089, as a biocontrol agent.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Trichoderma atraviride
<220> FEATURE:
<221> NAME/KEY: misc_feature
<222> LOCATION: (1)..(20)
<223> OTHER INFORMATION: PCR primer Ech42 gene

<400> SEQUENCE: 1
gttctgaggc tggaagttgc                                              20

<210> SEQ ID NO 2
<211> LENGTH: 20
<212> TYPE: DNA
<213> ORGANISM: Trichoderma atraviride
<220> FEATURE:
<221> NAME/KEY: misc_feature
<222> LOCATION: (1)..(20)
<223> OTHER INFORMATION: PCR primer Ech42 gene

<400> SEQUENCE: 2
acgccgtcta cttcaccaac                                              20

<210> SEQ ID NO 3
<211> LENGTH: 25
<212> TYPE: DNA
<213> ORGANISM: Trichoderma atraviride
```

```
<220> FEATURE:
<221> NAME/KEY: misc_feature
<222> LOCATION: (1)..(25)
<223> OTHER INFORMATION: Ech42 probe. Polymorphic nucleotides in
      position 9 , 20.

<400> SEQUENCE: 3
taccccttca atcaccaatt gttag                                          25

<210> SEQ ID NO 4
<211> LENGTH: 20
<212> TYPE: DNA
<213> ORGANISM: Trichoderma atraviride
<220> FEATURE:
<221> NAME/KEY: misc_feature
<222> LOCATION: (1)..(20)
<223> OTHER INFORMATION: PCR primer Tga3 gene.

<400> SEQUENCE: 4
tgttgaagca ttgggtttga                                                20

<210> SEQ ID NO 5
<211> LENGTH: 20
<212> TYPE: DNA
<213> ORGANISM: Trichoderma atraviride
<220> FEATURE:
<221> NAME/KEY: misc_feature
<222> LOCATION: (1)..(20)
<223> OTHER INFORMATION: PCR primer Tga3 gene

<400> SEQUENCE: 5
tgattgaggt gacgttctcg                                                20

<210> SEQ ID NO 6
<211> LENGTH: 23
<212> TYPE: DNA
<213> ORGANISM: Trichoderma atraviride
<220> FEATURE:
<221> NAME/KEY: misc_feature
<222> LOCATION: (1)..(23)
<223> OTHER INFORMATION: Tga3  probe

<400> SEQUENCE: 6
aaggagtgaa cgaaagaagt gga                                            23
```